(12) United States Patent
Minami

(10) Patent No.: US 11,066,446 B2
(45) Date of Patent: Jul. 20, 2021

(54) CYCLIC PEPTIDE, AFFINITY CHROMATOGRAPHY SUPPORT, LABELED ANTIBODY, ANTIBODY DRUG CONJUGATE, AND PHARMACEUTICAL PREPARATION

(71) Applicant: FUJIFILM Corporation, Tokyo (JP)

(72) Inventor: Koichi Minami, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/358,178

(22) Filed: Mar. 19, 2019

(65) Prior Publication Data

US 2019/0202864 A1   Jul. 4, 2019

Related U.S. Application Data

(63) Continuation of application No. PCT/JP2017/029517, filed on Aug. 17, 2017.

(30) Foreign Application Priority Data

Sep. 30, 2016 (JP) .............................. JP2016-194506
Jun. 14, 2017 (JP) .............................. JP2017-116490

(51) Int. Cl.
| | |
|---|---|
| C07K 7/64 | (2006.01) |
| C07K 16/06 | (2006.01) |
| C07K 1/22 | (2006.01) |
| B01J 20/285 | (2006.01) |
| A61K 47/68 | (2017.01) |
| B01D 15/38 | (2006.01) |
| A61K 47/65 | (2017.01) |

(52) U.S. Cl.
CPC ............... C07K 7/64 (2013.01); A61K 47/65 (2017.08); A61K 47/6889 (2017.08); B01D 15/3809 (2013.01); B01J 20/285 (2013.01); C07K 1/22 (2013.01); C07K 16/065 (2013.01); C07K 2319/30 (2013.01)

(58) Field of Classification Search
CPC ............... A61K 47/65; A61K 47/6889; B01D 15/3809; B01J 20/285; C07K 16/065; C07K 1/22; C07K 2319/30; C07K 7/08; C07K 7/64

See application file for complete search history.

(56) References Cited

U.S. PATENT DOCUMENTS

| | | | |
|---|---|---|---|
| 5,677,419 | A | 10/1997 | Bolin et al. |
| 2004/0087765 | A1 | 5/2004 | Ronspeck et al. |
| 2004/0253247 | A1 | 12/2004 | Dennis et al. |
| 2007/0160534 | A1 | 7/2007 | Dennis et al. |
| 2009/0326192 | A1 | 12/2009 | Nash et al. |
| 2010/0121039 | A1 | 5/2010 | Dennis et al. |
| 2011/0263479 | A1 | 10/2011 | Jacobsen et al. |
| 2014/0274790 | A1 | 9/2014 | Ito |
| 2014/0314670 | A1 | 10/2014 | D'Addona et al. |
| 2015/0078999 | A1* | 3/2015 | Heath ................ C07K 1/047 424/1.69 |
| 2016/0009760 | A1 | 1/2016 | Bittermann et al. |
| 2017/0334948 | A1 | 11/2017 | Bittermann et al. |
| 2018/0230184 | A1 | 8/2018 | Minami |
| 2019/0247827 | A1* | 8/2019 | Kihara ................ B01J 20/3274 |

(Continued)

FOREIGN PATENT DOCUMENTS

| | | |
|---|---|---|
| EP | 2749646 A1 | 7/2014 |
| JP | 2007-289200 A | 11/2007 |
| JP | 2015-509486 A | 3/2015 |

(Continued)

OTHER PUBLICATIONS

Hyo Jin Kang et al., "Cyclic peptide ligand with high binding capacity for affinity purification of immunoglobulin G", Journal of Chromatography A, Sep. 3, 2016, vol. 1466, pp. 105-112.

Yiyi Gong et al., "Development of the Double Cyclic Peptide Ligand for Antibody Purification and Protein Detection", Bioconjugate Chemistry, Jun. 30, 2016, vol. 27, pp. 1569-1573.

International Search Report for PCT/JP2017/029517, dated Nov. 14, 2017.

Written Opinion for PCT/JP2017/029517, dated Nov. 14, 2017.

International Preliminary Report on Patentability with the translation of Written Opinion dated Apr. 2, 2019, issued in application No. PCT/JP2017/029517.

Communication dated Apr. 28, 2020, from the Japanese Patent Office in application No. 2018-541980.

(Continued)

*Primary Examiner* — Marcela M Cordero Garcia

(74) *Attorney, Agent, or Firm* — Sughrue Mion, PLLC

(57) ABSTRACT

A cyclic peptide is represented by Formula (I),

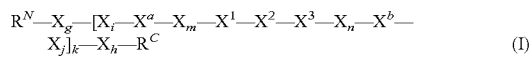

in Formula (I), $R^N$ represents an N-terminal group; $R^C$ represents a C-terminal group; $X^1$ represents an L-leucine residue, an L-isoleucine residue, an L-methionine residue, an L-lysine residue, or an L-arginine residue; $X^2$ represents an L-valine residue or an L-isoleucine residue; $X^3$ represents an L-tryptophan residue or an L-phenylalanine residue; one of $X^a$ and $X^b$ represents an amino acid residue derived from an amino acid having an azide group on a side chain and the other represents an amino acid residue derived from an amino acid having an alkynyl group on a side chain, and $X_g$, $X_h$, $X_i$, $X_j$, $X_m$, and $X_n$ each represent g consecutive X's, h consecutive X's, i consecutive X's, j consecutive X's, m consecutive X's, and n consecutive X's; X represents an amino acid residue.

16 Claims, No Drawings

Specification includes a Sequence Listing.

(56) References Cited

U.S. PATENT DOCUMENTS

2020/0040039 A1\* 2/2020 Inoue .................. C07K 7/64

FOREIGN PATENT DOCUMENTS

| JP | 2017-095443 A | 6/2017 |
| --- | --- | --- |
| RU | 2095368 C1 | 11/1997 |
| WO | 01/45746 A2 | 6/2001 |
| WO | 2008104000 A2 | 8/2008 |
| WO | 2012/113803 A1 | 8/2012 |
| WO | 2013/027796 A1 | 2/2013 |

OTHER PUBLICATIONS

Communication dated Mar. 6, 2020 from the Canadian Intellectual Property Office in CA Application No. 3,036,768.

Empting et al., ""Triazole Bridge": Disulfide-Bond Replacement by Ruthenium-Catalyzed Formation of 1,5-Disiibstltuted 1,2,3-Triazoles", Angew. Chem. Int. Ed., vol. 50, pp. 5207-5211, 2011, 5 pages total.

Thundimadathil, "Click chemistry in peptide science: a mini-reviewL: Synthesis of clickable peptides and applications", Monographic supplement series: Oligos & Peptides—Chimica Oggi—Chemistry Today, vol. 31, No. 2, Mar. 2013, 4 pages total.

Search Report dated Nov. 20, 2019 issued by the Federal Service on Intellectual Property of Russia in counterpart application No. 2019109008/10.

Extended European Search Report dated Nov. 26, 2019 issued by the European Patent Office in counterpart application No. 17855467.1.

Li et al., "Click Chemistry in Peptide-Based Drug Design", Molecules, 2013, vol. 18, pp. 9797-9817 (21 pages total).

Notification of Reason for Refusal, dated Jul. 1, 2020, issued by the Korean Intellectual Property Office in Application No. 10-2019-7008756.

Communication dated Oct. 2, 2020, issued by the European Patent Office in European Patent Application No. 17855467.1.

Isaad, A., et al., "Side chain-to-side chain cyclization by click reaction", Journal of Peptide Science, vol. 15, No. 7, Jul. 1, 2009, XP055141279, pp. 451-454.

Roice, M., et al., "High Capacity Poly(ethylene glycol) Based Amino Polymers for Peptide and Organic Synthesis", QSAR & Combinatorial Science, vol. 23, No. 8, Jan. 1, 2004, XP008041412, pp. 662-673.

Communication, dated Jan. 19, 2021, issued by the Korean Intellectual Property Office in Korean Patent Application No. 10-2019-7008756.

Communication, dated Feb. 8, 2021, issued by the Canadian Intellectual Property Office in application No. CA3036768.

Communication, dated Jun. 11, 2021, issued by the Indian Patent Office in corresponding Indian Patent Application No. 201947010403.

\* cited by examiner

CYCLIC PEPTIDE, AFFINITY CHROMATOGRAPHY SUPPORT, LABELED ANTIBODY, ANTIBODY DRUG CONJUGATE, AND PHARMACEUTICAL PREPARATION

CROSS-REFERENCE TO RELATED APPLICATIONS

This application is a Continuation of PCT International Application No. PCT/JP2017/029517 filed on Aug. 17, 2017, which claims priority under 35 U.S.C § 119(a) to Japanese Patent Application No. 2016-194506 filed on Sep. 30, 2016 and Japanese Patent Application No. 2017-116490 filed on Jun. 14, 2017. Each of the above application(s) is hereby expressly incorporated by reference, in its entirety, into the present application.

BACKGROUND OF THE INVENTION

1. Field of the Invention

The present invention relates to a cyclic peptide, an affinity chromatography support, a labeled antibody, an antibody drug conjugate, and a pharmaceutical preparation.

2. Description of the Related Art

Currently, antibody drugs are drawing attention as the most reliable molecular-targeted drugs and are rapidly broadening the field of new pharmaceutical products. In most of the antibody drugs that are being developed or marketed currently, antibodies belonging to the class of immunoglobulin G (IgG) are used.

In the related art, for the purification of IgG antibodies, proteins such as protein A or protein G derived from *Staphylococcus aureus* are used. Because these proteins also bind to IgG of a mouse and a rabbit, the proteins have been frequently used for IgG purification of reagents for research. In recent years, the antibody drugs mainly exploiting human IgG1 have been used, and accordingly, the importance of the proteins in the industrial and pharmaceutical use has increased further. Particularly, a protein A column is frequently used in the antibody drug purification. A purification system using the protein A column is introduced into many antibody drug manufacturing processes.

However, some problems have been pointed out for the protein A column. For example, there is a problem of mixing of protein A into purified antibodies. Protein A is a protein derived from bacteria, exhibits high immunogenicity after being administered into the human body, and can become endotoxin. Protein A as an affinity ligand in the purification of pharmaceutical products is required to be purified to a high degree so as to prevent the intermixing of undesirable substances. Therefore, the cost of the protein A column used for the purification of pharmaceutical products increases.

In order to solve the problem, a new IgG antibody purification system is being developed.

For example, US2004/0087765A describes an immunoglobulin-binding polypeptide which has an amino acid sequence of $R^1$-X01-X02-X03-X04-X05-X06-X07-X08-X09-X10-X11-X12-X13-$R^2$ and includes about 11 to 13 residues. US2004/0087765A describes that the polypeptide may be a cyclic peptide cyclized by forming a disulfide bond (in a case where X02=X12=C) or an amide bond (in a case where one of X02 and X12 is Dpr, Dab, K, or Orn and the other is D or E; here, Dab represents diaminobutanoic acid, Dpr represents diaminopropionic acid, and Orn represents ornithine) between X02 and X12 (<0017> to <0034>).

Furthermore, WO2013/027796A describes an IgG-binding polypeptide which is represented by $(X_{1-3})$—C—$(X_2)$—H—R-G-(Xaa1)-L-V—W—C—$(X_{1-3})$ and includes 13 to 17 amino acid residues. WO2013/027796A describes that the polypeptide may be a cyclic peptide in which a disulfide bond is formed between two cysteine (C) residues (<0042> to <0044>).

Moreover, JP2007-289200A describes an IgG-Fc-binding peptide which has Formula $Xaa_1$-$Xaa_2$-$Xaa_3$-$Xaa_4$-Cys-$Xaa_5$-$Xaa_6$-$Xaa_7$-$Xaa_8$-Gly-Glu-Leu-Val-Trp-Cys-$Xaa_9$-$Xaa_{10}$-$Xaa_{11}$-$Xaa_{12}$-$Xaa_{13}$ and has 11 to 20 amino acids (claim 39). JP2007-289200A describes that the peptide can be cyclized by the formation of a disulfide bond or a lactam bond, the residues which can form a disulfide bond include Cys, Pen, Mpr, Mpp, and the like, and the residues which can form a lactam bond include Asp, Glu, Lys, Orn, αβ-diaminobutyric acid, diaminoacetic acid, aminobenzoic acid, mercaptobenzoic acid, and the like (<0039>).

SUMMARY OF THE INVENTION

Focusing on improving the antibody binding properties by controlling the steric structure, the inventor of the present invention examined the binding activity and the chemical resistance of the antibody binding cyclic peptides described in US2004/0087765A, WO2013/027796A, and JP2007-289200A. As a result, the inventor found that the binding activity and the chemical resistance of the peptides need to be further improved.

An object of the present invention is to provide a cyclic peptide having excellent antibody binding properties and improved chemical resistance.

In order to achieve the aforementioned object, the inventor of the present invention repeated intensive examinations. As a result, the inventor found that the amino acid residues in cross-linked portions play important roles for the chemical resistance, and accomplished the present invention.

That is, the present invention provides [1] to [20] described below.

[1] A cyclic peptide represented by Formula (I).

$$R^N-X_g-[X_i-X^a-X_m-X^1-X^2-X^3-X_n-X^b-X_j]_k-X_h-R^C \qquad (I)$$

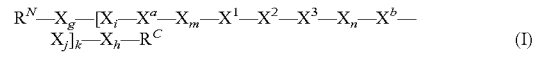

In Formula (I), $R^N$ represents an N-terminal group;

$R^C$ represents a C-terminal group;

$X^1$ represents an L-leucine residue, an L-isoleucine residue, an L-methionine residue, an L-lysine residue, or an L-arginine residue;

$X^2$ represents an L-valine residue or an L-isoleucine residue;

$X^3$ represents an L-tryptophan residue or an L-phenylalanine residue;

one of $X^a$ and $X^b$ represents an amino acid residue derived from an amino acid having an azide group on a side chain and the other represents an amino acid residue derived from an amino acid having an alkynyl group on a side chain, and $X^a$ and $X^b$ are bonded to each other through a triazole bond;

$X_g$, $X_h$, $X_i$, $X_j$, $X_m$, and $X_n$ each represent g consecutive X's, h consecutive X's, i consecutive X's, j consecutive X's, m consecutive X's, and n consecutive X's;

X represents an amino acid residue, and in a case where there is a plurality of X's, the plurality of X's may be the same as or different from each other;

g, h, i, and j each independently represent an integer equal to or greater than 0; m and n are integers satisfying 0≤m≤9, 0≤n≤9, and 3≤m+n≤9 simultaneously; and k is an integer equal to or greater than 1, and in a case where k≥2, $X^1$, $X^2$, $X^3$, $X^a$, $X^b$, $X_i$, $X_j$, $X_m$, and $X_n$ in a repeating unit $[X_i-X^a-X_m-X^1-X^2-X^3-X_n-X^b-X_j]$ each may be the same or different between the repeating units.

[2] The cyclic peptide described in [1] that is represented by Formula (IA).

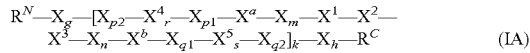  (IA)

In Formula (IA), $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I);

$X^4_r$, $X^5_s$, $X_{p1}$, $X_{p2}$, $X_{q1}$, and $X_{q2}$ each represent r consecutive $X^4$'s, s consecutive $X^5$'s, p1 consecutive X's, p2 consecutive X's, q1 consecutive X's, and q2 consecutive X's;

$X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}-X^4_r-X_{p1}-X^a-X_m-X^1-X^2-X^3-X_n-X^b-X_{q1}-X^5_s-X_{q2}]$ each may be the same or different between the repeating units.

[3] The cyclic peptide described in [1] that is represented by Formula (IB).

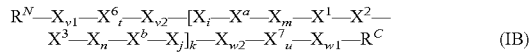  (IB)

In Formula (IB), $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I);

$X^6_t$, $X^7_u$, $X_{v1}$, $X_{v2}$, $X_{w1}$, and $X_{w2}$ each represent t consecutive $X^6$'s, u consecutive $X^7$'s, v1 consecutive X's, v2 consecutive X's, w1 consecutive X's, and w2 consecutive X's;

$X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other;

t and u each represent an integer satisfying 0≤t≤5, 0≤u≤5, and 1≤Max (t,u)≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≥2, $X^1$, $X^2$, $X^3$, $X^a$, $X^b$, $X_i$, $X_j$, $X_m$, and $X_n$ in a repeating unit $[X_i-X^a-X_m-X^1-X^2-X^3-X_n-X^b-X_j]$ each may be the same or different between the repeating units.

[4] The cyclic peptide described in any one of [1] to [3] that is represented by Formula (IC).

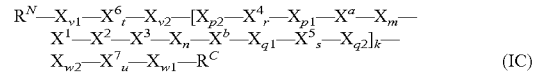  (IC)

In Formula (IC), $R^N$, $R^C$, $X^1$, $X^2$, $X^3$, $X^a$, $X^b$, $X_m$, $X_n$, X, m, n, and k have the same definitions as those in Formula (I);

$X_{p1}$, $X_{p2}$, $X_{q1}$, $X_{q2}$, $X^4_r$, $X^5_s$, $X^6_t$, $X^7_u$, $X_{v1}$, $X_{v2}$, $X_{w1}$, and $X_{w2}$ each represent p1 consecutive X's, p2 consecutive X's, q1 consecutive X's, q2 consecutive X's, r consecutive $X^4$'s, s consecutive $X^5$'s, t consecutive $X^6$'s, u consecutive $X^7$'s, v1 consecutive X's, v2 consecutive X's, w1 consecutive X's, and w2 consecutive X's;

$X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other;

$X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s;

t and u each represent an integer satisfying 0≤t≤5, 0≤u≤5, and 1≤Max (t,u)≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}-X^4_r-X_{p1}-X^a-X_m-X^1-X^2-X^3-X_n-X^b-X_{q1}-X^5_s-X_{q2}]$ each may be the same or different between the repeating units.

[5] The cyclic peptide described in [2] or [4], in which the amino acid having a carboxy group on a side chain is at least one of amino acid selected from the group consisting of L-aspartic acid, D-aspartic acid, L-glutamic acid, D-glutamic acid, L-homoglutamic acid, and D-homoglutamic acid, and the amino acid having a hydroxy group on a side chain is at least one of amino acid selected from the group consisting of L-serine, D-serine, L-homoserine, D-homoserine, L-tyrosine, D-tyrosine, L-threonine, D-threonine, L-allothreonine, and D-allothreonine.

[6] The cyclic peptide described in [3] or [4], in which the amino acid having an immobilizing functional group on a side chain is at least one of amino acid selected from the group consisting of L-lysine, D-lysine, L-cysteine, D-cysteine, L-homocysteine, and D-homocysteine.

[7] The cyclic peptide described in any one of [1] to [6], in which the amino acid having an azide group on a side chain is at least one of amino acid selected from the group consisting of β-azide-L-alanine, γ-azide-L-homoalanine, δ-azide-L-norvaline, and ε-azide-L-lysine, and the amino acid having an alkynyl group on a side chain is at least one of amino acid selected from the group consisting of L-propargylglycine, L-homopropargylglycine, and L-bishomopropargylglycine.

[8] The cyclic peptide described in any one of [1] to [7], in which $X_m$—$X^1$—$X^2$—$X^3$—$X_n$ and an amino acid sequence (SEQ ID NO: 1) represented by Formula (1) or an amino acid sequence (SEQ ID NO: 2) represented by Formula (2) share sequence homology equal to or higher than 70%.

A-Y—H-L$^1$-G-E-L$^2$-V—W (1)

A-Y—H—R-G-E-L$^2$-V—W (2)

In Formula (1) and Formula (2),
A represents an L-alanine residue or a D-alanine residue;
Y represents an L-tyrosine residue or a D-tyrosine residue;
H represents an L-histidine residue or a D-histidine residue;
L$^1$ represents an L-leucine residue or a D-leucine residue;
R represents an L-arginine residue or a D-arginine residue;
G represents a glycine residue;
E represents an L-glutamic acid residue or a D-glutamic acid residue;
L$^2$ represents an L-leucine residue;
V represents an L-valine residue; and
W represents an L-tryptophan residue.

[9] The cyclic peptide described in any one of [1] to [8], in which k=1.

[10] The cyclic peptide described in [1] that is represented by Formula (II).

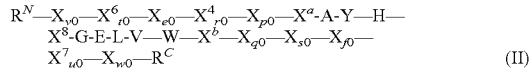

$R^N$—$X_{v0}$—$X^6_{t0}$—$X_{e0}$—$X^4_{r0}$—$X_{p0}$—$X^a$-A-Y—H—
$X^8$-G-E-L-V—W—$X^b$—$X_{q0}$—$X_{s0}$—$X_{f0}$—
$X^7_{u0}$—$X_{w0}$—$R^C$ (II)

In Formula (II),
$X^a$, $X^b$, X, $R^N$, and $R^C$ have the same definitions as those in Formula (I);
$X^4$ and $X^5$ each independently represent an L-amino acid residue or a D-amino acid residue having a carboxy group or a hydroxy group on a side chain, and in a case where there is a plurality of $X^4$'s or $X^5$'s, the plurality of $X^4$'s or $X^5$'s may be the same as or different from each other;
$X^6$ and $X^7$ each independently represent an L-amino acid residue or a D-amino acid residue having an immobilizing functional group on a side chain, and in a case where there is a plurality of $X^6$'s or $X^7$'s, the plurality of $X^6$'s or $X^7$'s may be the same as or different from each other;
$X^8$ represents any one residue selected from the group consisting of an L-leucine residue, an L-arginine residue, a D-leucine residue, and a D-arginine residue;
e0 and f0 each represent an integer satisfying $0 \le e0 \le 10$ and $0 \le f0 \le 10$;
p0 and q0 each represent an integer satisfying $0 \le p0 \le 5$ and $0 \le q0 \le 5$;
r0 and s0 each represent an integer satisfying $0 \le r0 \le 5$ and $0 \le s0 \le 5$;
t0 and u0 each represent an integer satisfying $0 \le t0 \le 5$ and $0 \le u0 \le 5$;
v0 and w0 each represent an integer satisfying $0 \le v0 \le 5$ and $3 \le w0 \le 5$;
p0, q0, r0, s0, t0, u0, v0, and w0 satisfy $0 \le p0+q0+r0+s0+t0+u0+v0+w0 \le 39$;
A represents an L-alanine residue or a D-alanine residue;
Y represents an L-tyrosine residue or a D-tyrosine residue;

H represents an L-histidine residue or a D-histidine residue;
G represents a glycine residue;
E represents an L-glutamic acid residue or a D-glutamic acid residue;
L represents an L-leucine residue;
V represents an L-valine residue; and
W represents an L-tryptophan residue.

[11] The cyclic peptide described in any one of [1] to [10] that is an antibody binding ligand.

[12] The cyclic peptide described in any one of [1] to [10] that is a linker for labeling antibodies.

[13] The cyclic peptide described in any one of [1] to [10] that is a linker for antibody drug conjugates.

[14] The cyclic peptide described in any one of [1] to [10] that is a drug carrier.

[15] An affinity chromatography support comprising a water insoluble carrier and the cyclic peptide described in any one of [1] to [10], in which the water insoluble carrier and the cyclic peptide are directly or indirectly bonded to each other.

[16] A labeled antibody comprising an antibody, a labeling compound, and the cyclic peptide described in any one of [1] to [10], in which the antibody and the labeling compound are bonded to each other through the cyclic peptide.

[17] An antibody drug conjugate comprising an antibody, a drug, and the cyclic peptide described in any one of [1] to [10], in which the antibody and the drug are bonded to each other through the cyclic peptide.

[18] The antibody drug conjugate described in [17], in which the drug is a drug having undergone liposomization, polymer micellization, or PEGylation.

[19] A pharmaceutical preparation comprising a drug and the cyclic peptide described in any one of [1] to [10], in which the drug and the cyclic peptide are directly or indirectly bonded to each other.

[20] The pharmaceutical preparation described in [19], in which the drug is a drug having undergone liposomization, polymer micellization, or PEGylation.

According to the present invention, there is provided a cyclic peptide having excellent antibody binding properties and improved chemical resistance.

DESCRIPTION OF THE PREFERRED EMBODIMENTS

[Cyclic Peptide]

First, the characteristics of the present invention that are not found in the related art will be described.

US2004/0087765A, WO2013/027796A, and JP2007-289200A describe cyclic peptides cyclized by forming a disulfide bond between two cysteine residues. According to the results of evaluating the relative binding activity and the chemical resistance in Comparative Example 2 which will be described later, although the antibody binding properties of the cyclic peptides cyclized by forming a disulfide bond between two cysteine residues are excellent, the chemical resistance thereof is poor, and hence a desired performance cannot be obtained.

US2004/0087765A describes a cyclic peptide cyclized by forming an amide bond between two amino acid residues through a reaction between a side-chain amino group and a side-chain carboxy group. JP2007-289200A describes a cyclic peptide cyclized by forming a lactam bond (amide bond) between an N-terminal amino group or a side-chain amino group and a side-chain carboxy group. According to the results of evaluating the relative binding activity and the chemical resistance in Comparative Example 1 which will be described later, although the chemical resistance of the cyclic peptide cyclized by the amide bond between a side-chain amino group and a side-chain carboxy group is excellent, the antibody binding properties thereof are poor, and hence a desired performance cannot be obtained.

On the contrary, in the present invention, because the constitutions which will be described later are adopted, a cyclic peptide having excellent antibody binding properties and improved chemical resistance could be obtained.

In the present specification, a range described using "to" means a range which includes both ends before and after "to". For example, "A to B" means a range including A and B. Furthermore, a range described using "equal to or greater than n" or "equal to or smaller than n" means a range including numbers equal to or greater than n or a range including numbers equal to or smaller than n. For example, "equal to or greater than C" means a range including C and numbers greater than C, and "equal to or smaller than D" means a range including D and numbers smaller than D.

In the present invention, in principle, amino acids are described using names, codes, and the like adopted by INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Biochemical Nomenclature (JCBN). Furthermore, amino acid residues are described using the codes of amino acids from which the amino acid residues are derived. The amino acid residues include N-terminal amino acid residues (referred to as "N-terminal residues" as well) and C-terminal amino acid residues (referred to as "C-terminal residues" as well).

Unless otherwise specified, the amino acid sequence (referred to as "primary structure") of a peptide or a protein is described by aligning amino acid residues in a line, such that the left end of the line becomes the N-terminal and the right end of the line becomes the C-terminal. In a case where an amino acid residue in the amino acid sequence of a peptide or a protein is identified, including the position thereof, sometimes a number showing which position the amino acid residue occupies from the N-terminal side is placed on the right side of the code of the amino acid residue. For example, the second L-lysine from the N-terminal is described as Lys2 in some cases.

In a case where an amino acid is described using its name, and the amino acid includes isomers having an enantiomeric relationship, that is, in a case where the amino acid includes an L-isomer and a D-isomer, except for a case where the L-isomer and the D-isomer are clearly differentiated from each other, the amino acid represents the L-isomer in principle. For example, "isoleucine" represents "L-isoleucine", and the enantiomer of "isoleucine" represents "D-isoleucine". The same is true for amino acid residues.

In a case where an amino acid is described using its code (three-letter code or one-letter code), and the amino acid includes isomers having an enantiomeric relationship, that is, in a case where the amino acid includes an L-isomer and a D-isomer, except for a case where the L-isomer and the D-isomer are clearly differentiated from each other, the amino acid represents the L-isomer in principle. Here, "X" representing any amino acid is not limited thereto. For example, "Lys" and "L-Lys" both represent "L-lysine", and "D-Lys" represents "D-lysine". The same is true for amino acid residues.

In a case where an amino acid is described using its name, and the amino acid includes isomers having a diastereomeric relationship, the isomers are not included in the amino acid specified by its name. A diastereomer is described using a prefix "allo" and regarded as a different kind of amino acid. For example, "threonine" and "L-threonine" do not include "L-allothreonine", and "D-threonine" does not include "D-allothreonine". The same is true for amino acid residues.

Table 1 shows the names and the codes (one-letter code and three-letter code) of amino acids having officially recognized one-letter codes and three-letter codes.

TABLE 1

| One-letter code | Three-letter code | Name |
|---|---|---|
| A | Ala | L-Alanine |
| B | Asx | L-Aspartic acid or L-Asparagine |
| C | Cys | L-Cysteine |
| D | Asp | L-Aspartic acid |
| E | Glu | L-Glutamic acid |
| F | Phe | L-Phenylalanine |
| G | Gly | Glycine |
| H | His | L-Histidine |
| I | Ile | L-Isoleucine |
| K | Lys | L-Lysine |
| L | Leu | L-Leucine |
| M | Met | L-Methionine |
| N | Asn | L-Asparagine |
| O | Pyl | L-Pyrrolysine |
| P | Pro | L-Proline |
| Q | Gln | L-Glutamine |
| R | Arg | L-Arginine |
| S | Ser | L-Serine |
| T | Thr | L-Threonine |
| U | Sec | L-Selenocysteine |
| V | Val | L-Valine |
| W | Trp | L-Tryptophan |
| X | Xaa | Any amino acid |
| Y | Tyr | L-Tyrosine |
| Z | Glx | L-Glutamic acid or L-Glutamine |

The amino acids are not limited to those listed in Table 1, and the amino acids referred to as unusual amino acid can also be used. Examples of unusual amino acids are listed in Table 2 shown below, but the present invention is not limited thereto.

TABLE 2

| Three-letter code | Name |
|---|---|
| Aad | Homoglutamic acid |
| βAad | 3-Aminoadipic acid |
| Abu | 2-Aminobutanoic acid |
| A2bu | 2,4-Diaminobutanoic acid |
| Ahx | 2-Aminohexanoic acid |
| Ahe | 2-Aminoheptanoic acid |
| Aib | 2-Aminoisobutyric acid |
| εAhx | 6-Aminohexanoic acid |
| βAla | β-Alanine |
| Ape | 2-Aminopentanoic acid |
| A2pr | 2,3-Diaminopropanoic acid |
| Apm | 2-Aminopimelic acid |
| A2pm | 2,6-Diaminopimelic acid |
| Cit | Citrulline |
| Cya | Cysteic acid |
| Dbu | 2,4-Diaminobutanoic acid |
| Dpm | 2,6-Diaminopimelic acid |
| Dpr | 2,3-Diaminopropanoic acid |
| Gla | 4-Carboxyglutamic acid |
| Glp | 5-Oxoproline |
| Hcy | Homocysteine |
| Hse | Homoserine |
| Hsl | Homoserine lactone |
| 5Hyl | 5-Hydroxylysine (Hyl) |

TABLE 2-continued

| Three-letter code | Name |
| --- | --- |
| aHyl | allo-Hydroxylysine |
| 3Hyp | 3-Hydroxyproline |
| 4Hyp | 4-Hydroxyproline |
| aIle | allo-Isoleucine |
| Nle | Norleucine |
| Nva | Norvaline |
| Orn | Ornithine |
| Sar | Sarcosine |
| aThr | allo-Threonine |
| Thx | Thyroxine |

Hereinafter, the cyclic peptide according to the embodiment of the present invention will be specifically described.

The cyclic peptide according to the embodiment of the present invention is a cyclic peptide represented by Formula (I).

$$R^N-X_g-[X_i-X^a-X_m-X^1-X^2-X^3-X_n-X^b-X_j]_k-X_h-R^C \quad (I)$$

In Formula (I), for example, $X_n$ means that n X's are linked to each other. In other words, $X_n$ means $-(X)_n-$. $X_g$, $X_h$, $X_i$, $X_j$, and $X_m$ mean the same thing as $X_n$.

Regarding the cyclic peptide according to the embodiment of the present invention, in a polypeptide chain, a ring portion closed by cross-linking is referred to as a cyclic portion, and a portion which is not included in the cyclic portion is referred to as a linear portion.

Furthermore, in the cyclic portion, a portion forming a cross-linked structure in the molecule of the cyclic peptide according to the embodiment of the present invention is referred to as a cross-linked portion, and a portion greatly favoring the antibody binding properties of the cyclic peptide according to the embodiment of the present invention is referred to as an antibody binding portion.

In the cyclic peptide represented by Formula (I), "$X^a-X_m-X^1-X^2-X^3-X_n-X^b$" is a cyclic portion, "$X_g$", "$X_h$", "$X_i$", and "$X_j$" are linear portions, "$X^a$" and "$X^b$" are cross-linked portions, and "$X^1-X^2-X^3$" is an antibody binding portion.

In Formula (I), $[X_i-X^a-X_m-X^1-X^2-X^3-X_n-X^b-X_j]$ is referred to as a repeating portion in some cases.

In Formula (I), $X^1$ is an L-leucine residue, an L-isoleucine residue, an L-methionine residue, an L-lysine residue, or an L-arginine residue. $X^1$ is preferably an L-leucine residue or an L-isoleucine residue, and more preferably an L-leucine residue.

In Formula (I), $X^2$ is an L-valine residue or an L-isoleucine residue, and preferably an L-valine residue.

In Formula (I), $X^3$ is an L-tryptophan residue or an L-phenylalanine residue, and preferably an L-tryptophan residue.

In Formula (I), one of $X^a$ and $X^b$ is an amino acid residue derived from an amino acid having an azide group on a side chain and the other is an amino acid residue derived from an amino acid having an alkynyl group on a side chain. $X^a$ and $X^b$ are bonded to each other through a triazole bond. In the present invention, in some cases, the amino acid having an azide group on a side chain is referred to as "azide group-containing amino acid", and the amino acid having an alkynyl group on a side chain is referred to as "alkynyl group-containing amino acid".

The triazole bond is a bond formed of an azide group and an alkynyl group by the Huisgen reaction represented by the following formula.

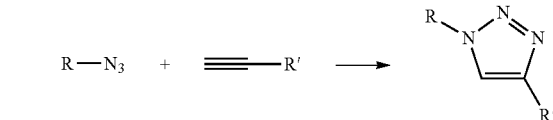

In the above formula, R represents a portion other than the azide group in the azide group-containing amino acid residue (amino acid residue having an azide group on a side chain), and R' represents a portion other than the ethynyl group in the alkynyl group-containing amino acid residue (amino acid residue having an alkynyl group on a side chain).

In the amino acid having an azide group on a side chain, the side chain is preferably represented by Formula (a).

In Formula (a), $R^{11}$ represents an alkylene group having 1 to 10 carbon atoms, preferably represents an alkylene group having 1 to 6 carbon atoms, more preferably represents a methylene group, an ethylene group, a propane-1,3-diyl group, a propane-1,2-diyl group, a butane-1,2-diyl group, a butane-1,3-diyl group, a butane-1,4-diyl group, or a butane-2,3-diyl group, and even more preferably represents a methylene group, an ethylene group, or a butane-1,4-diyl group. From the viewpoint of economic efficiency or cross-linking reaction properties, the side chain is preferably a short chain but is not limited for this reason.

In addition to "$-N_3$", "$-N=N^+=N^-$", "$-N^--N^+\equiv N$", and the like are used to describe an azide group in some cases.

In the amino acid having an alkynyl group on a side chain, the side chain is preferably represented by Formula (b).

In Formula (b), $R^{12}$ represents an alkylene group having 1 to 10 carbon atoms, preferably represents an alkylene group having 1 to 6 carbon atoms, more preferably represents a methylene group, an ethylene group, a propane-1,3-diyl group, a propane-1,2-diyl group, a butane-1,2-diyl group, a butane-1,3-diyl group, a butane-1,4-diyl group, or a butane-2,3-diyl group, even more preferably represents a methylene group, an ethylene group, or a propane-1,2-diyl group, and still more preferably represents a methylene group or an ethylene group. From the viewpoint of economic efficiency or cross-linking reaction properties, the side chain is preferably a short chain but is not limited for this reason.

It is preferable that one of $X^a$ and $X^b$ is an amino acid residue derived from β-azide-L-alanine, γ-azide-L-homoalanine, δ-azide-L-norvaline, or ε-azide-L-lysine, and the other is an amino acid residue derived from L-propargylglycine, L-homopropargylglycine, or L-bishomopropargylglycine. It is more preferable that one of $X^a$ and $X^b$ is an amino acid residue derived from β-azide-L-alanine, γ-azide-L-homoalanine, δ-azide-L-norvaline, or ε-azide-L-lysine, and the other is an amino acid residue derived from L-homopropargylglycine or L-bishomopropargylglycine. It is even more preferable that one of $X^a$ and $X^b$ is an amino acid residue derived from β-azide-L-alanine, γ-azide-L-homoalanine, or ε-azide-L-lysine, and the other is an amino acid residue derived from L-homopropargylglycine or L-bishomopropargylglycine.

In Formula (I), in a case where X represents an amino acid residue, and there is a plurality of X's, the plurality of X's may be the same as or different from each other.

X is not particularly limited as long as it is an amino acid residue. X is preferably an amino acid residue derived from an amino acid selected from the group consisting of amino acids (excluding B, Z, and X) shown in Table 1 and amino acids shown in Table 2, and more preferably an amino acid residue derived from an amino acid selected from the group consisting of amino acids (excluding B, Z, and X) shown in Table 1. In a case where there is an enantiomer or a diastereomer of these amino acids, X may be an amino acid residue derived from the enantiomer or the diastereomer.

In Formula (I), $R^N$ represents an N-terminal group.

Examples of the N-terminal group include an amino group, and the amino group may have undergone N-terminal modification such as N-acetylation, N-formylation, or N-acylation.

In Formula (I), $R^C$ represents a C-terminal group.

Examples of the C-terminal group include a carboxy group, and the carboxy group may have undergone C-terminal modification such as amidation.

In Formula (I), g and h each independently represent an integer equal to or greater than 0.

g preferably satisfies $0 \le g \le 20$, more preferably satisfies $0 \le g \le 10$, and even more preferably satisfies $0 \le g \le 5$.

h preferably satisfies $0 \le h \le 20$, more preferably satisfies $0 \le h \le 10$, and even more preferably satisfies $0 \le h \le 5$.

In Formula (I), i and j each independently represent an integer equal to or greater than 0.

i preferably satisfies $0 \le i \le 20$, more preferably satisfies $0 \le i \le 10$, and even more preferably satisfies $0 \le i \le 5$.

j preferably satisfies $0 \le j \le 20$, more preferably satisfies $0 \le j \le 10$, and even more preferably satisfies $0 \le j \le 5$.

In Formula (I), m and n are integers satisfying $0 \le m \le 9$ and $0 \le n \le 9$.

m and n satisfy $3 \le m+n \le 9$, preferably satisfy $4 \le m+n \le 8$, and more preferably satisfy $5 \le m+n \le 7$.

In Formula (I), the number of amino acid residues [(m+n+5) residues] in the cyclic portion [$X^a$—$X_m$—$X^1$—$X^2$—$X^3$—$X_n$—$X^b$] is 8 to 14, preferably 9 to 13, and more preferably 10 to 12.

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide according to the embodiment of the present invention become excellent.

k is an integer satisfying $k \ge 1$. k preferably satisfies $1 \le k \le 3$, more preferably satisfies $1 \le k \le 2$, and even more preferably satisfies $k=1$.

Although the number of repeating units is not particularly limited, the larger the number of repeating units, the more the cyclic portions can be included in the cyclic peptide.

Accordingly, it is possible to improve the antibody binding properties of the cyclic peptide.

The smaller the number of repeating units, the further the total number of amino acid residues can be reduced. Accordingly, it is possible to inhibit the antigenicity of the cyclic peptide.

From the viewpoint the synthesis cost of the cyclic peptide, it is preferable that the number of amino acid residues and the number of repeating units are small.

In a case where $k \ge 2$, that is, in a case where the cyclic peptide represented by Formula (I) includes two or more repeating units [$X_i$—$X^a$—$X_m$—$X^1$—$X^2$—$X^3$—$X_n$—$X^b$—$X_j$], $X^1$, $X^2$, $X^3$, $X^a$, $X^b$, $X_i$, $X_j$, $X_m$, and $X_n$ in the repeating unit each may be the same or different between the repeating units.

The total number of amino acid residues in the cyclic peptide represented by Formula (I) is preferably 8 to 50, more preferably 9 to 40, even more preferably 10 to 30, and still more preferably 10 to 20.

That is, in Formula (I), g, h, i, j, m, n, and k preferably satisfy $8 \le g+h+(i+j+m+n+5) \times k \le 50$, more preferably satisfy $9 \le g+h+(i+j+m+n+5) \times k \le 40$, even more preferably satisfy $10 \le g+h+(i+j+m+n+5) \times k \le 30$, and still more preferably satisfy $10 \; g+h+(i+j+m+n+5) \times k \le 20$.

Generally, the larger the number of amino acid residues, the higher the manufacturing cost. Therefore, from the viewpoint of economic efficiency, it is preferable that the total number of amino acid residues is small.

The molecular weight of the cyclic peptide represented by Formula (I) is not particularly limited. However, from the viewpoint of antigenicity, the molecular weight of the cyclic peptide according to the embodiment of the present invention is preferably about equal to or smaller than 5,000, more preferably about equal to or smaller than 4,000, even more preferably about equal to or smaller than 3,000, and most preferably about equal to or smaller than 2,000. "About" means that the molecular weight includes a margin of ±2%.

The cyclic peptide according to the embodiment of the present invention is preferably a cyclic peptide represented by Formula (IA).

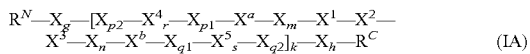

$R^N$—$X_g$—[$X_{p2}$—$X^4_r$—$X_{p1}$—$X^a$—$X_m$—$X^1$—$X^2$—$X^3$—$X_n$—$X^b$—$X_{q1}$—$X^5_s$—$X_{q2}$]$_k$—$X_h$—$R^C$ (IA)

In Formula (IA), all of $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I).

In Formula (IA), similarly to $X_n$ in Formula (I), $X_n$ means that n X's are linked to each other. The same is true for $X_m$, $X_{p1}$, $X_{p2}$, $X_{q1}$, and $X_{q2}$.

In Formula (IA), $X^4_r$ and $X^5_s$ each mean that r $X^4$'s are linked to each other, and s $X^5$'s are linked to each other.

In the cyclic peptide represented by Formula (IA), "$X_g$", "$X_h$", "$X_{p2}$—$X^4_r$,$X_{p1}$", and "$X_{q1}$—$X^5_s$—$X_{q2}$" are linear portions. The cyclic portion, the cross-linked portion, and the antibody binding portion are the same as those in the cyclic peptide represented by Formula (I).

In Formula (IA), [$X_{p2}$—$X^4_r$—$X_{p1}$—$X^a$—$X_m$—$X^1$—$X^2$—$X^3$—$X_n$—$X^b$—$X_{q1}$—$X^5_s$—$X_{q2}$] is a repeating unit.

In Formula (IA), $X^4$ and $X^5$ each independently represent an amino acid residue derived from an amino acid having a carboxy group on a side chain or an amino acid residue derived from an amino acid having a hydroxy group on a side chain.

Examples of the amino acid having a carboxy group on a side chain include L-aspartic acid, D-aspartic acid, L-glutamic acid, D-glutamic acid, L-homoglutamic acid, D-homoglutamic acid, and the like.

Examples of the amino acid having a hydroxy group on a side chain include L-serine, D-serine, L-homoserine, D-homoserine, L-tyrosine, D-tyrosine, L-threonine, D-threonine, L-allothreonine, D-allothreonine, and the like.

$X^4$ and $X^5$ preferably each independently represent an amino acid residue selected from the group consisting of an L-serine residue, a D-serine residue, an L-homoserine residue, a D-homoserine residue, an L-aspartic acid residue, a D-aspartic acid residue, an L-glutamic acid residue, a D-glutamic acid residue, an L-homoglutamic acid residue, a D-homoglutamic acid residue, an L-tyrosine residue, a D-tyrosine residue, an L-homotyrosine residue, a D-homotyrosine residue, an L-threonine residue, a D-threonine residue, an L-allothreonine residue, and a D-allothreonine residue, and more preferably each independently represent an amino acid residue selected from the group consisting of an L-aspartic acid residue, a D-aspartic acid residue, an L-threonine residue, and a D-threonine residue. It is even more preferable that $X^4$ represents an L-aspartic acid residue and $X^5$ represents an L-threonine residue.

It is considered that in a case where $X^4$ and $X^5$ each independently represent an amino acid residue derived from an amino acid having a carboxy group on a side chain or an amino acid residue derived from an amino acid having a hydroxy group on a side chain, due to a hydrogen bond and/or an electrostatic interaction, the interaction between the antibody binding portion of the cyclic portion and an antibody can become stronger, and hence the antibody binding properties are improved.

In Formula (IA), p1, p2, q1, and q2 each independently represent an integer equal to or greater than 0.

p1 preferably satisfies 0≤p1≤20, more preferably satisfies 0≤p1≤10, even more preferably satisfies 0≤p1≤5, and still more preferably satisfies 0≤p1≤2.

p2 preferably satisfies 0≤p2≤20, more preferably satisfies 0≤p2≤10, even more preferably satisfies 0≤p2≤5, and still more preferably satisfies 0≤p2≤2.

q1 preferably satisfies 0≤q1≤20, more preferably satisfies 0≤q1≤10, even more preferably satisfies 0≤q1≤5, and still more preferably satisfies 0≤q1≤2.

q2 preferably satisfies 0≤q2≤20, more preferably satisfies 0≤q2≤10, even more preferably satisfies 0≤q2≤5, and still more preferably satisfies 0≤q2≤2.

In Formula (IA), r and s each represent an integer satisfying 0≤r≤5, 0≤s≤5, and 1≤Max (r,s)≤5. r and s preferably each represent an integer satisfying 0≤r≤4, 0≤s≤4, and 1≤Max (r,s)≤4, and more preferably each represent an integer satisfying 0≤r≤3, 0≤s≤3, and 1≤Max (r,s)≤3.

Max (r,s) represents a larger one between two numbers represented by r and s in a case where r≠s and represents r or s in a case where r=s.

In Formula (IA), the number of amino acid residues [(m+n+5) residues] in the cyclic portion [$X^a$—$X_m$—$X^1$—$X^2$—$X^3$—$X_n$—$X^b$] is 8 to 14, preferably 9 to 13, and more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide according to the embodiment of the present invention become excellent.

In a case where k≥2, that is, in a case where the cyclic peptide represented by Formula (IA) includes two or more repeating units [$X_{p2}$—$X^4_r$—$X_{p1}$—$X^a$—$X_m$—$X^1$—$X^2$—$X^3$—$X_n$—$X^b$—$X_{q1}$—$X^5_s$—$X_{q2}$], $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in the repeating unit each may be the same or different between the repeating units.

The total number of amino acid residues in the cyclic peptide represented by Formula (IA) is preferably 8 to 50, more preferably 9 to 40, even more preferably 10 to 30, and still more preferably 10 to 20.

That is, in Formula (IA), g, h, m, n, p1, p2, q1, q2, r, s, and k preferably satisfy 8≤g+h+(m+n+p1+p2+q1+q2+r+s+5)×k≤50, more preferably satisfy 9≤g+h+(m+n+p1+p2+q1+q2+r+s+5)×k≤40, even more preferably satisfy 10≤g+h+(m+n+p1+p2+q1+q2+r+s+5)×k≤30, and still more preferably satisfy 10≤g+h+(m+n+p1+p2+q1+q2+r+s+5)×k≤20.

Generally, the larger the number of amino acid residues, the higher the manufacturing cost. Therefore, from the viewpoint of economic efficiency, it is preferable that the total number of amino acid residues is small.

The cyclic peptide according to the embodiment of the present invention is preferably a cyclic peptide represented by Formula (IB).

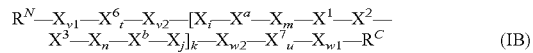

(IB)

In Formula (IB), all of $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I).

In Formula (IB), similarly to $X_n$ in Formula (I), $X_n$ means that n X's are linked to each other. The same is true for $X_m$, $X_{v1}$, $X_{v2}$, $X_{w1}$, and $X_{w2}$.

In Formula (IB), $X^6_t$ and $X^7_u$ each mean that t $X^6$'s are linked to each other, and u $X^7$'s are linked to each other.

In the cyclic peptide represented by Formula (IB), "$X_i$", "$X_j$", "$X_{v1}$—$X^6_t$—$X_{v2}$", and "$X_{w2}$—$X^7_u$—$X_{w1}$" are linear portions. The cyclic portion, the cross-linked portion, and the antibody binding portion are the same as those in the cyclic peptide represented by Formula (I).

In Formula (IB), [$X_i$—$X^a$—$X_m$—$X^1$—$X^2$—$X^3$—$X_n$—$X^b$—$X_j$] is a repeating unit, similarly to Formula (I).

In Formula (IB), $X^6$ and $X^7$ each independently represent an amino acid residue derived from an amino acid having an immobilizing functional group on a side chain. In a case where there is a plurality of $X^6$'s or $X^7$'s, the plurality of $X^6$'s or $X^7$'s may be the same as or different from each other.

The aforementioned "immobilizing functional group" is a functional group which can form a covalent bond by reacting with a functional group on a support. The "support" will be described later.

Examples of the immobilizing functional group include an amino group, a carboxy group, a hydroxy group, a thiol group, an aldehyde group (formyl group), a carbamoyl group, an azide group, an alkynyl group, and the like.

Examples of the combination of the immobilizing functional group that the cyclic peptide according to the embodiment of the present invention has and the functional group on the support include an amino group and a carboxy group (amide bond forming reaction), an amino group and an aldehyde group (reductive amination reaction), an amino group and an epoxy group, a hydroxy group and an epoxy group, a carboxy group and a hydroxy group (ester bond forming reaction), a thiol group and a thiol group (disulfide bond), a thiol group and an epoxy group, an azide group and an alkynyl group (Huisgen cycloaddition reaction), and the like.

In a case where the immobilizing functional group that the cyclic peptide according to the embodiment of the present invention has and the functional group on the support form a covalent bond by reacting with each other, the cyclic peptide according to the embodiment of the present invention is immobilized on the support. At least some of the immobilizing functional groups that the cyclic peptide according to the embodiment of the present invention has may form a covalent bond by reacting with the functional group on the support, and it is not necessary for all the immobilizing functional groups to react with the functional group on the support.

In the aforementioned amino acid having an immobilizing functional group on a side chain, the immobilizing functional group is preferably at least one of functional group selected from the group consisting of an amino group, a thiol group, and an aldehyde group, and more preferably at least one of functional group selected from the group consisting of an amino group and a thiol group.

The amino acid having an immobilizing functional group on a side chain is preferably at least one of amino acid selected from the group consisting of L-lysine, D-lysine, L-cysteine, D-cysteine, L-homocysteine, and D-homocysteine.

In a case where an amino group is used as the immobilizing functional group, the amino group can be bonded to a carboxy group on the support through an amide bond, and the cyclic peptide according to the embodiment of the present invention as an affinity ligand can be easily immobilized.

In a case where a thiol group is used as the immobilizing functional group, the thiol group can be bonded to an epoxy group on the support through a covalent bond, and the cyclic peptide according to the embodiment of the present invention as an affinity ligand can be easily immobilized.

Examples of the amino acid having an amino group on a side chain include L-lysine, D-lysine, and the like, and examples of the amino acid having a thiol group on a side chain include L-cysteine and D-cysteine. Because these amino acids are relatively cheap, the manufacturing cost of the cyclic peptide according to the embodiment of the present invention can be reduced. Therefore, from the viewpoint of economic efficiency, these amino acids are preferable.

In the present invention, "support" refers to a substrate on which the cyclic peptide according to the embodiment of the present invention can be immobilized. The support has a functional group which can form a covalent bond by reacting with the immobilizing functional group that the cyclic peptide according to the embodiment of the present invention has. The functional group is appropriately selected according to the immobilizing functional group.

Examples of the material constituting the support include polysaccharides such as agarose, dextran, starch, cellulose, pullulan, chitin, chitosan, cellulose triacetate, and cellulose diacetate, derivatives of these, vinyl-based polymers such as polyacrylamide, polymethacrylamide, polyacrylate, polymethacrylate, polyalkyl vinyl ether, and polyvinyl alcohol, and the like. These materials may form a cross-linked structure because then mechanical strength can be secured. It is preferable that the support is formed of one of material or two or more of materials among these.

The support is preferably a porous support, more preferably a porous film or a porous particle, and even more preferably a porous particle.

In Formula (IB), t and u each represent an integer satisfying $0 \le t \le 5$, $0 \le u \le 5$, and $1 \le \text{Max}(t,u) \le 5$, preferably each represent an integer satisfying $0 \le t \le 4$, $0 \le u \le 4$, and $1 \le \text{Max}(t,u) \le 4$, and more preferably each represent an integer satisfying $0 \le t \le 3$, $0 \le u \le 3$, and $1 \le \text{Max}(t,u) \le 3$.

Max (t,u) represents a larger one between two numbers represented by t and u in a case where $t \ne u$ and represents t or u in a case where $t = u$.

In Formula (IB), v1, v2, w1, and w2 each independently represent an integer equal to or greater than 0.

v1 preferably satisfies $0 \le v1 \le 20$, more preferably satisfies $0 \le v1 \le 10$, even more preferably satisfies $0 \le v1 \le 5$, and still more preferably satisfies $0 \le v1 \le 2$.

v2 preferably satisfies $0 \le v2 \le 20$, more preferably satisfies $0 \le v2 \le 10$, even more preferably satisfies $0 \le v2 \le 5$, and still more preferably satisfies $0 \le v2 \le 2$.

w1 preferably satisfies $0 \le w1 \le 20$, more preferably satisfies $0 \le w1 \le 10$, even more preferably satisfies $0 \le w1 \le 5$, and still more preferably satisfies $0 \le w1 \le 2$.

w2 preferably satisfies $0 \le w2 \le 20$, more preferably satisfies $0 \le w2 \le 10$, even more preferably satisfies $0 \le w2 \le 5$, and still more preferably satisfies $0 \le w2 \le 2$.

In Formula (IB), the number of amino acid residues [(m+n+5) residues] in the cyclic portion $[X^a-X_m-X^1-X^2-X^3-X_n-X^b]$ is 8 to 14, preferably 9 to 13, and more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide according to the embodiment of the present invention become excellent.

In a case where $k \ge 2$, that is, in a case where the cyclic peptide represented by Formula (IB) includes two or more repeating units $[X_i-X^a-X_m-X^1-X^2-X^3-X_n-X^b-X_j]$, $X^1$, $X^2$, $X^3$, $X^a$, $X^b$, $X_m$, $X_n$, $X_i$, and $X_j$ in the repeating unit each may be the same or different between the repeating units.

The total number of amino acid residues in the cyclic peptide represented by Formula (IB) is preferably 8 to 50, more preferably 9 to 40, even more preferably 10 to 30, and still more preferably 10 to 20.

That is, in Formula (IB), i, j, m, n, t, u, v1, v2, w1, w2, and k preferably satisfy $8 \le (i+j+m+n+5) \times k+t+u+v1+v2+w1+w2 \le 50$, more preferably satisfy $9 \le (i+j+m+n+5) \times k+t+u+v1+v2+w1+w2 \le 40$, even more preferably satisfy $10 \le (i+j+m+n+5) \times k+t+u+v1+v2+w1+w2 \le 30$, and still more preferably satisfy $10 \le (i+j+m+n+5) \times k+t+u+v1+v2+w1+w2 \le 20$.

Generally, the larger the number of amino acid residues, the higher the manufacturing cost. Therefore, from the viewpoint of economic efficiency, it is preferable that the total number of amino acid residues is small.

The cyclic peptide according to the embodiment of the present invention is more preferably a cyclic peptide represented by Formula (IC).

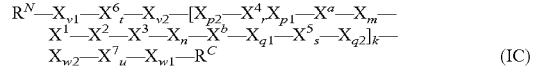

$$R^N-X_{v1}-X^6{}_t-X_{v2}-[X_{p2}-X^4{}_r-X_{p1}-X^a-X_m-X^1-X^2-X^3-X_n-X^b-X_{q1}-X^5{}_s-X_{q2}]_k-X_{w2}-X^7{}_u-X_{w1}-R^C \quad (IC)$$

In Formula (IC), all of $R^N$, $R^C$, $X^1$, $X^2$, $X^3$, $X^a$, $X^b$, $X_m$, $X_n$, X, m, n, and k have the same definitions as those in Formula (I), all of $X^4$, $X^5$, p1, p2, q1, q2, r, and s have the same definitions as those in Formula (IA), and all of $X^6$, $X^7$, t, u, v1, v2, w1, and w2 have the same definitions as those in Formula (IB).

In Formula (IC), similarly to $X_n$ in Formula (I), $X_n$ means that n X's are linked to each other. The same is true for $X_m$, $X_{p1}$, $X_{p2}$, $X_{q1}$, $X_{q2}$, $X_{v1}$, $X_{v2}$, $X_{w1}$, and $X_{w2}$.

In Formula (IC), $X^4{}_r$, $X^5{}_s$, $X^6{}_t$, and $X^7{}_u$ each mean that r $X^4$'s are linked to each other, s $X^5$'s are linked to each other, t $X^6$'s are linked to each other, and u $X^7$'s are linked to each other.

In the cyclic peptide represented by Formula (IC), "$X_{v1}-X^6{}_t-X_{v2}$", "$X_{w2}-X^7{}_u-X_{w1}$", "$X_{p2}-X^4{}_r-X_{p1}$", and "$X_{q1}-X^5{}_s-X_{q2}$" are linear portions. The cyclic portion, the cross-linked portion, and the antibody binding portion are the same as those in the cyclic peptide represented by Formula (I).

In Formula (IC), $[X_{p2}-X^4{}_r-X_{p1}-X^a-X_m-X^1-X^2-X^3-X_n-X^b-X_{q1}-X^5{}_s-X_{q2}]$ is a repeating unit, similarly to Formula (IA).

In Formula (IC), the number of amino acid residues [(m+n+5) residues] in the cyclic portion $[X^a-X_m-X^1-X^2-X^3-X_n-X^b]$ is 8 to 14, preferably 9 to 13, and even more preferably 10 to 12, similarly to Formula (I).

In a case where the number of amino acid residues in the cyclic portion is within the above range, the intramolecular strain of the cyclic peptide does not excessively increase, and the high-order structure such as α-helix is stabilized. Therefore, the antibody binding properties of the cyclic peptide according to the embodiment of the present invention become excellent.

In a case where k≥2, that is, in a case where the cyclic peptide represented by Formula (IC) includes two or more repeating units $[X_{p2}-X^4_r-X_{p1}-X^a-X_m-X^1-X^2-X^3-X_n-X^b-X_{q1}-X^5_s-X_{q2}]$, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in the repeating unit each may be the same or different between the repeating units.

The total number of amino acid residues in the cyclic peptide represented by Formula (IC) is preferably 8 to 50, more preferably 9 to 40, even more preferably 10 to 30, and still more preferably 10 to 20.

That is, in Formula (IC), m, n, p1, p2, q1, q2, r, s, t, u, v1, v2, w1, w2, and k preferably satisfy $8 \leq (m+n+p1+p2+q1+q2+r+s+5) \times k+t+u+v1+v2+w1+w2 \leq 50$, more preferably satisfy $9 \leq (m+n+p1+p2+q1+q2+r+s+5) \times k+t+u+v1+v2+w1+w2 \leq 40$, even more preferably satisfy $10 \leq (m+n+p1+p2+q1+q2+r+s+5) \times k+t+u+v1+v2+w1+w2 \leq 30$, and still more preferably satisfy $10 \leq (m+n+p1+p2+q1+q2+r+s+5) \times k+t+u+v1+v2+w1+w2 \leq 20$.

Generally, the larger the number of amino acid residues, the higher the manufacturing cost. Therefore, from the viewpoint of economic efficiency, it is preferable that the total number of amino acid residues is small.

The portion represented by $X_m-X^1-X^2-X^3-X_n$ in Formula (I), (IA), (IB), or (IC) and an amino acid sequence (SEQ ID NO: 1) represented by Formula (1) or an amino acid sequence (SEQ ID NO: 2) represented by Formula (2) preferably share sequence homology equal to or higher than 70%, more preferably share sequence homology equal to or higher than 75%, even more preferably share sequence homology equal to or higher than 85%, and still more preferably share sequence homology equal to or higher than 90%.

A-Y—H-L¹-G-E-L²-V—W  (1)

A-Y—H—R-G-E-L²-V—W  (2)

In Formula (1) and Formula (2), A represents an L-alanine residue or a D-alanine residue; Y represents an L-tyrosine residue or a D-tyrosine residue; H represents an L-histidine residue or a D-histidine residue; L¹ represents an L-leucine residue or a D-leucine residue; R represents an L-arginine residue or a D-arginine residue; G represents a glycine residue; E represents an L-glutamic acid residue or a D-glutamic acid residue; L² represents an L-leucine residue; V represents an L-valine residue; and W represents an L-tryptophan residue.

The sequence homology between two amino acid sequences is determined as below.

(i) Performing Alignment of Two Amino Acid Sequences

By assigning a score of +1 to matches, a score of −1 to mismatches, and a score of −1 to gaps, alignment is performed such that the alignment score is maximized.

(ii) Calculating Sequence Homology

Based on the obtained alignment, the sequence homology is calculated by the following expression.

Sequence homology[%]=(number of matching positions/total number of positions)×100[%]

The total number of positions is the length of an alignment, and the number of matching positions is the number of positions in which the types of amino acids are matched.

Whether or not the types of amino acid residues are matched is determined according to whether or not the structure of a side chain of an amino acid (amino acid side chain) from which the amino acid residues are derived is the same. The structures of side chains of amino acids having an enantiomeric relationship are not the same as each other.

(iii) Calculation Example of Sequence Homology

For example, suppose that there are amino acid sequences shown below.

Sequence A                    (SEQ ID NO: 1)
AYHRGELVW

Sequence B                    (SEQ ID NO: 22)
AWHLGELVW

In a case where alignment is performed under the conditions described above, the following result is obtained. Herein, the sites where the types of amino acids (residues) are the same between the sequences A and B are marked with a homology string "|" such that the sites are easily recognized. Furthermore, "−" is a gap.

SequenceA    A Y H R G E L V W
             |   | | | | | |
SequenceB    A W H L G E L V W The scores of this alignment is matches (+1)×7+mismatches (−1)×2+gaps (−1)×0=5.

In this example, the total number of positions is 9, the number of matching positions is 7. Therefore, the sequence homology calculated according to the above expression is 7/9×100=77.8%.

In the present invention, k in Formulae (I) and (IA) to (IC) is preferably 1.

In a case where the cyclic peptide has one cyclic portion-including portion, the total length of the cyclic peptide can be shortened, and hence the cyclic peptide is easily synthesized. Furthermore, by the Huisgen reaction at the time of cyclization, it is possible to avoid the formation of a cross-link at an unintended site.

The cyclic peptide according to the embodiment of the present invention is particularly preferably a cyclic peptide represented by Formula (II).

$R^N-X_{v0}-X^6_{t0}-X_{e0}-X^4_{r0}-X_{p0}-X^a\text{-A-Y}-H-$
$X^8\text{-G-E-L-V}-W-X^b-X_{q0}-X^5_{s0}-X_{f0}-$
$X^7_{u0}-X_{w0}-R^C$  (II)

In Formula (II), $X^a$, $X^b$, X, $R^N$, and $R^C$ have the same definitions as those in Formula (I).

Furthermore, in Formula (II), $X_{e0}$ means e0 X's linked to each other similarly to $X_n$ in Formula (I). The same is true for $X_{f0}$, $X_{p0}$, $X_{q0}$, $X_{v0}$, and $X_{w0}$.

In the cyclic peptide represented by Formula (II), "$X^a$-A-Y—H—$X^8$-G-E-L-V—W—$X^b$" is a cyclic portion, "$X_{v0}-X^6_{t0}-X_{e0}-X^4_{r0}-X_{p0}-$" and "$X_{q0}-X^5_{s0}-X_{f0}-X^7_{u0}-X_{w0}-$" are linear portions, "$X^a$" and "$X^b$" are cross-linked portions, and "L-V—W" is an antibody binding portion.

In Formula (II), $X^4$ and $X^5$ have the same definitions as those in Formula (IA).

In Formula (II), $X^6$ and $X^7$ have the same definitions as those in Formula (IB).

In Formula (II), e0 and f0 each represent an integer satisfying 0≤e0≤10 and 0≤f0≤10.

e0 preferably satisfies 0≤e0≤5, more preferably satisfies 0≤e0≤3, and even more preferably satisfies 0≤e0≤2.

f0 preferably satisfies 0≤f0≤5, more preferably satisfies 0≤f0≤3, and even more preferably satisfies 0≤f0≤2.

In Formula (II), p0 and q0 each represent an integer satisfying 0≤p0≤5 and 0≤q0≤5.

p0 preferably satisfies 0≤p0≤3, and more preferably satisfies 0≤p0≤2.

q0 preferably satisfies 0≤q0≤3, and more preferably satisfies 0≤q0≤2.

That is, in Formula (II), e0, f0, p0, q0, r0, s0, t0, u0, v0, and w0 satisfy 0≤e0+f0+p0+q0+r0+s0+t0+u0+v0+w0≤39, preferably satisfy 0≤e0+f0+p0+q0+r0+s0+t0+u0+v0+w0≤29, more preferably satisfy 0≤e0+f0+p0+q0+r0+s0+t0+u0+v0+w0≤19, and even more preferably satisfy 0≤e0+f0+p0+q0+r0+s0+t0+u0+v0+w0≤9.

Particularly preferable examples of the cyclic peptide according to the embodiment of the present invention are represented by the Formulae (3) to (18) (SEQ ID NOS: 3 to 18).

```
Asp-[Lys(N3)]-Ala-Tyr-His-Arg-Gly-Glu-Leu-Val-Trp-[Bpg]-Thr-Lys-Lys    (3)

Asp-[Lys(N3)]-Ala-Tyr-His-Leu-Gly-Glu-Leu-Val-Trp-[Bpg]-Thr-Lys-Lys    (4)

Asp-[Bpg]-Ala-Tyr-His-Leu-Gly-Glu-Leu-Val-Trp-[Lys(N3)]-Thr-Lys-Lys    (5)

Asp-[HPG]-Ala-Tyr-His-Leu-Gly-Glu-leu-Val-Trp-[Ala(N3)]-Thr-Lys-Lys    (6)

Lys-Lys-Lys-Asp-+Hpg+-Ala-Tyr-His-Leu-Gly-Glu-Leu-Val-Trp-[Ala(N3)]-Thr  (7)

Asp-[Abu(N3)]-Ala-Tyr-His-Arg-Gly-Glu-Leu-Val-Trp-[Pra]-Thr-Lys-Lys    (8)

Asp-[Abu(N3)]-Ala-Tyr-His-Leu-Gly-Glu-Leu-Val-Trp-[Pra]-Thr-Lys-Lys    (9)

Asp-[Lys(N3)]-Ala-Tyr-His-Leu-Gly-Glu-Leu-Val-Trp-[Hpg]-Thr-Lys-Lys    (10)

Asp-[Pra]-Ala-Tyr-His-Leu-Gly-Glu-Leu-Val-Trp-[Lys(N3)]-Thr-Lys-Lys    (11)

Asp-[Lys(N3)]-Ala-Tyr-His-Leu-Gly-Glu-Leu-Val-Trp-[Pra]-Thr-Lys-Lys    (12)

Asp-[Abu(N3)]-Ala-Tyr-His-Leu-Gly-Glu-Leu-Val-Trp-[Hpg]-Thr-Lys-Lys    (13)

Asp-[Hpg]-Ala-Tyr-His-Leu-Gly-Glu-Leu-Val-Trp-[Abu(N3)]-Thr-Lys-Lys    (14)

Asp-[Abu(N3)]-Ala-Tyr-His-Leu-Gly-Glu-Leu-Val-Trp-[Bpg]-Thr-Lys-Lys    (15)

Asp-[Bpg]-Ala-Tyr-His-Leu-Gly-Glu-Leu-Val-Trp-[Nva(N3)]-Thr-Lys-Lys    (16)

Asp-[Hpg]-Ala-Tyr-His-Leu-Gly-Glu-Leu-Val-Trp-[Nva(N3)]-Thr-Lys-Lys    (17)

Asp-[Nva(N3)]-Ala-Tyr-His-Leu-Gly-Glu-Leu-Val-Trp-[Bpg]-Thr-Lys-Lys    (18)
```

In Formula (II), r0 and s0 each represent an integer satisfying 0≤r0≤5 and 0≤s0≤5.

r0 preferably satisfies 0≤r0≤3, and more preferably satisfies 0≤r0≤2.

s0 preferably satisfies 0≤s0≤3, and more preferably satisfies 0≤s0≤2.

In Formula (II), t0 and u0 each represent an integer satisfying 0≤t0≤5 and 0≤u0≤5.

t0 preferably satisfies 0≤t0≤3, and more preferably satisfies 0≤t0≤2.

u0 preferably satisfies 0≤u0≤3, and more preferably satisfies 0≤u0≤2.

In Formula (II), v0 and w0 each represent an integer satisfying 0≤v0≤5 and 3≤w0≤5.

v0 preferably satisfies 0≤v0≤3, and more preferably satisfies 0≤v0≤2.

w0 preferably satisfies 0≤w0≤3, and more preferably satisfies 0≤w0≤2.

In Formula (II), A represents an L-alanine residue or a D-alanine residue; Y represents an L-tyrosine residue or a D-tyrosine residue; H represents an L-histidine residue or a D-histidine residue; G represents a glycine residue; E represents an L-glutamic acid residue or a D-glutamic acid residue; V represents an L-valine residue; and W represents an L-tryptophan residue.

In Formula (II), the total number of amino acid residues in the cyclic peptide is 11 to 50, preferably 11 to 40, more preferably 11 to 30, and even more preferably 11 to 20.

In Formulae (3) to (18), [Ala(N3)] represents an amino acid residue derived from β-azide-L-alanine, [Abu(N3)] represents an amino acid residue derived from γ-azide-L-homoalanine, [Nva(N3)] represents an amino acid residue derived from δ-azide-L-norvaline, [Lys(N3)] represents an amino acid residue derived from ε-azide-L-lysine, [Pra] represents an amino acid residue derived from L-propargylglycine, [Hpg] represents L-homopropargylglycine, and [Bpg] represents L-bishomopropargylglycine.

A triazole bond represented by the following formula is formed between [Ala(N3)], [Abu(N3)], [Nva(N3)], or [Lys(N3)] and [Pra], [Hpg], or [Bpg]. In the following formula, "*" represents a point of binding to an adjacent amino acid residue, x is an integer of 1 to 4, and y is an integer of 1 to 3.

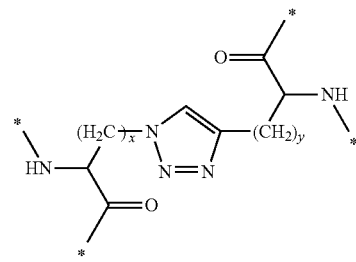

The method for identifying the structure of the cyclic peptide according to the embodiment of the present invention is not particularly limited. For example, by appropriately combining a protein sequencer (referred to as peptide sequencer as well), mass spectrometry, a nuclear magnetic resonance method, and X-ray crystallography, the structure including a primary structure can be determined. The mass spectrometry may be combined with a field desorption (FD) ionization method, a fast atom bombardment (FAB) ionization method, an electrospray ionization (ESI) method, a matrix-assisted laser desorption ionization (MALDI) method, and the like.

The cyclic peptide according to the embodiment of the present invention has excellent antibody binding properties. The antibody binding properties refer to binding activity with respect to antibodies and/or antibody derivatives. The higher the binding activity is, the more the antibodies are adsorbed onto the cyclic peptide in a case where the cyclic peptide is used as an affinity ligand for affinity chromatography for antibody purification, and hence a large amount of antibodies can be purified at a time. An antibody refers to immunoglobulin or an analogue, a fragment, or a conjugate of the antibody. The analogue refers to a natural protein or protein conjugate or to an artificially prepared protein or protein conjugate which keeps the structure or function of immunoglobulin in at least a portion thereof. The fragment refers to a protein which is prepared by an enzymatic treatment or designed by genetic engineering and has a partial structure of immunoglobulin. The conjugate refers to a protein prepared by fusing a functional portion of proteins having a biological activity such as various cytokines or cytokine receptors with the entirety or a portion of immunoglobulin through genetic engineering. The antibody is preferably a monoclonal antibody or a conjugate having an Fc region of immunoglobulin, and more preferably a monoclonal antibody. In the present invention, the immunoglobulin may be of any of five classes (isotypes) including immunoglobulin G (IgG), immunoglobulin M (IgM), immunoglobulin A (IgA), immunoglobulin D (IgD), and immunoglobulin E (IgE). Among these, IgG or IgM is preferable, and IgG is more preferable.

The cyclic peptide according to the embodiment of the present invention has excellent temporal stability or chemical resistance. Particularly, the cyclic peptide according to the embodiment of the present invention has excellent alkali resistance and reductant resistance. Because the cyclic peptide has excellent chemical resistance, for example, in a case where an affinity chromatography support, in which the cyclic peptide according to the embodiment of the present invention is used as an affinity ligand, is used for antibody purification, even though the support is repeatedly washed with a chemical, particularly, an alkali, the antibody binding properties are maintained. Therefore, the antibody purification cost can be further reduced.

[Method for Synthesizing Cyclic Peptide]

The method for synthesizing the cyclic peptide according to the embodiment of the present invention is not particularly limited. For example, the cyclic peptide can be synthesized by a peptide synthesis method based on synthetic organic chemistry or by a peptide synthesis method based on genetic engineering.

As the peptide synthesis method based on synthetic organic chemistry, any of a liquid-phase synthesis method and a solid-phase synthesis method can be used. As the method for synthesizing the polypeptide of the present invention, a solid-phase synthesis method in which a full automatic peptide synthesis device is used is preferable because this method is convenient.

The peptide synthesis method based on genetic engineering is a method of synthesizing a peptide by introducing a gene into a cell. As the cell, bacteria, eelworm cells, insect cells, mammal cells, animal cells, and the like are used.

For example, by introducing a non-natural amino acid into a cell by using a four-base codon method, the cyclic peptide can be synthesized. Furthermore, by synthesizing a linear peptide and causing cyclization by reacting a cross-linking functional group on a side chain of an amino acid residue introduced into a cyclic portion, the cyclic peptide can be synthesized.

For synthesizing the cyclic peptide according to the embodiment of the present invention, as a cross-linking functional group, an azide group and an alkynyl group are used. For synthesizing a polypeptide chain containing an amino acid residue into which an azide group or an alkynyl group is introduced, it is possible to use a method of incorporating an amino acid, into which an azide group or an alkynyl group is introduced, into a polypeptide chain at the time of synthesizing peptide or a method of synthesizing a polypeptide chain and then introducing an azide group or an alkynyl group into a side chain of a desired amino acid residue. Any of these methods may be used.

After the synthesis of a polypeptide chain containing an amino acid residue into which an azide group or an alkynyl group is introduced, by the Huisgen reaction, an addition reaction between the alkynyl group and the azide group is caused such that the amino acid residues are cross-linked. The Huisgen reaction is a 1,3-dipolar cycloaddition reaction by which 1,2,3-triazole is formed from azide (compound having —N=N$^+$=N$^-$ atomic group) and alkyne (carbon-carbon triple bond compound). The azide group and the alkynyl group are inert with respect to many functional groups or biomolecules, and the reaction generating a triazole ring from the azide group and the alkynyl group is a useful reaction in terms of exothermic thermodynamics. In the Huisgen reaction, it is preferable to use a copper catalyst because the reaction rate greatly increases in the presence of a copper catalyst, but it is not necessary to use such a catalyst.

[Use of Cyclic Peptide]

The cyclic peptide according to the embodiment of the present invention can be used as an antibody binding ligand, a linker for labeling antibodies, a linker for an antibody drug conjugate, a drug carrier (linker for pharmaceutical products), and the like, but the use of the cyclic peptide is not limited to these.

<Antibody Binding Ligand and Affinity Chromatography Support>

The cyclic peptide according to the embodiment of the present invention can be used as an antibody binding ligand in the technical field of affinity chromatography.

Examples of applications of the cyclic peptide according to the embodiment of the present invention used as an antibody binding ligand include an antibody or antibody derivative adsorbing material in which the cyclic peptide according to the embodiment of the present invention is immobilized on a water insoluble carrier and an affinity chromatography support.

"Water insoluble carrier" refers to a carrier (support) which is substantially insoluble in water. Examples of such a carrier include polysaccharides such as crystalline cellulose, cross-linked cellulose, cross-linked agarose, cross-linked dextran, and cross-linked pullulan, organic carriers such as an acrylate-based polymer and a styrene-based polymer, inorganic carriers such as glass beads and silica gel, composite carriers such as an organic-organic composite carriers and an organic-inorganic composite carriers obtained by combining the above carriers, and the like. From the viewpoint of alkali resistance, as the water insoluble carrier, polysaccharides or an acrylate-based polymer is more preferable, and polysaccharides such as agarose or cellulose are more preferable. Examples of commercial products that can be used as the water insoluble carrier include porous cellulose gel such as Cellufine GCL2000 (manufactured by JNC Corporation) (CELLUFINE is a registered trademark) and Cellfine MAX (manufactured by JNC Corporation), Sephacryl S-1000 SF (manufactured by GE Healthcare) obtained by cross-linking allyl dextran to methylenebisacrylamide through a covalent bond (SEPHACRYL is a registered trademark), acrylate-based supports such as TOYOPEARL (manufactured by Tosoh Corporation) (TOYOPEARL is a registered trademark), TOYOPEARL AF-Carboxy-650 (manufactured by Tosoh Corporation), and TOYOPEARL GigaCap CM-650 (manufactured by Tosoh Corporation), an agarose-based cross-linked support such as Sepharose CL4B (manufactured by GE Healthcare) (SEPHAROSE is a registered trademark), polymethcrylamide activated by an epoxy group such as Eupergit C250L (manufactured by Sigma-Aldrich Co., LLC.) (EUPERGIT is a registered trademark), and the like. Here, the water insoluble carrier in the present invention is not limited to the carriers or the activated carriers described above. Considering the purpose of use of the water insoluble carrier and how to use the water insoluble carrier, it is preferable that the water insoluble carrier used in the present invention has a large surface area and is a porous support having a number of pores with an appropriate size. The shape of the carrier is not particularly limited. The carrier can be any of a bead-like carrier, a fibrous carrier, a film-like carrier, and hollow fibrous carrier, and it is possible to select any shape.

The method for immobilizing the cyclic peptide according to the embodiment of the present invention on the water insoluble carrier is not particularly limited. For example, generally, it is possible to adopt a method that is adopted in a case where a protein or a polypeptide is immobilized on a carrier.

For example, the cyclic peptide can be immobilized by a method of activating a carrier by reacting the carrier with cyanogen bromide, epichlorohydrin, diglycidyl ether, tosyl chloride, tresyl chloride, hydrazine, and the like or introducing a reactive functional group into the surface of the carrier and immobilizing the carrier by reacting the carrier with a compound immobilized as a ligand, or a method of causing condensation by adding a condensation reagent such as carbodiimide or a reagent having a plurality of functional groups in a molecule such as glyceraldehyde to a system including a support and a compound immobilized as a ligand and cross-linking the condensate.

In the present invention, "ligand" refers to a molecule which has a certain degree of affinity with a specific substance and binds to the substance. The specific substance is not particularly limited, and is preferably an antibody or an antibody derivative. The binding site at which the ligand binds to an antibody or an antibody derivative is not particularly limited.

From the viewpoint of versatility, the binding site is preferably a constant region of an antibody or an antibody derivative. The constant region is not particularly limited, and is preferably fragment crystallizable (Fc) regions, constant regions of a light chain (CL regions), or constant regions of a heavy chain (CH regions). In the present invention, the ligand which can bind to an antibody or an antibody derivative is referred to as "antibody binding ligand" in some cases.

At the time of immobilizing a ligand on a support, it is preferable to dissolve (disperse) the ligand in an aqueous solvent (aqueous dispersion medium) or an organic solvent (organic dispersion medium). The aqueous solvent (aqueous dispersion medium) is not particularly limited, and examples thereof include a 4-(2-hydroxyethyl)-1-piperazineethane-sulfonic acid (HEPES) buffer solution, an acetic acid buffer solution, a phosphoric acid buffer solution, a citric acid buffer solution, a tris-hydrochloric acid buffer solution, and the like. The organic solvent (organic dispersion medium) is not particularly limited. The organic solvent is particularly preferably an organic polar solvent such as dimethyl sulfoxide (DMSO), N,N-dimethylformamide (DMF), or alcohol, and examples thereof include methanol, ethanol, isopropyl alcohol (IPA), 2,2,2-trifluoroethanol (TFE), 1,1,1,3,3,3-hexafluoro-2-propanol (HFIP), and the like.

The pH condition at the time of immobilizing the ligand is not particularly limited, and any of acidic, neutral, and alkaline conditions can be adopted. For example, the pH condition can be appropriately set according to the solvent (dispersion medium) to be used.

For example, in a case where the pH condition needs to be made alkaline, a base such as diazabicycloundecene (DBU) may be added to dimethyl sulfoxide (DMSO) or an alcohol.

In a case where the aforementioned adsorbing material is used as a filler for affinity chromatography, the density of antibody binding ligands is not particularly limited. However, the density is preferably 0.1 to 1,000 mmol/1 L of filler, more preferably 0.1 to 100 mmol/1 L of filler, and even more preferably 0.5 to 20 mmol/1 L of filler. In a case where the density is within the above range, the amount of the antibody binding ligand used and the antibody purification performance are balanced well, and it is possible to efficiently purify antibodies at lower costs.

<Linker for Labeling Antibodies and Labeled Antibody>

In the technical field of immunoassay, the cyclic peptide according to the embodiment of the present invention can be used as a linker for labeling antibodies.

Examples of applications of the cyclic peptide according to the embodiment of the present invention used as the linker for labeling antibodies include a labeled antibody which includes an antibody, a labeling compound, and the cyclic peptide according to the embodiment of the present invention and in which the antibody and the labeling compound are bonded to each other through the cyclic peptide according to the embodiment of the present invention.

Immunoassay is an analysis method for detecting or quantifying a trace substance by using an immune reaction (antigen-antibody reaction), and features high specificity and high sensitivity.

In the immunoassay, in order to detect an antibody (primary antibody) having bonded to a trace substance (antigen), a method of directly labeling the primary antibody, a method of labeling an antibody (secondary antibody) binding to the primary antibody, and the like are used. The cyclic peptide according to the embodiment of the present invention can be used as a linker for causing a labeling substance to bind to a primary antibody or as a linker for causing a labeling substance to bind to a secondary antibody. The cyclic peptide according to the embodiment of the present invention has antibody binding properties (immunoglobulin G (IgG) binding properties). Therefore, the labeled cyclic peptide according to the embodiment of the present invention can also be used instead of a labeled secondary antibody.

There are various labels. A system in which a radioisotope is used as a label is called radioimmunoassay (RIA), a system in which an enzyme such as peroxidase is used as a label is called enzyme immunoassay (EIA), a system in which a chemiluminescent substance such as luminol is used as a label is called chemiluminescent immunoassay (CLIA), and a system in which a fluorescent substance (fluorescent dye) such as fluorescein isothiocyanate (FITC) is used as a labeling substance is called fluorescent immunoassay (FIA). The cyclic peptide according to the embodiment of the present invention can be used as a linker for labeling antibodies in any of the systems.

In order to improve the detection sensitivity of immunoassay, a number of labels need to be attached to one antibody molecule. With the linker for labeling antibodies of the related art, in a case where a number of the linkers bind to an antibody, the antibody binding activity deteriorates. Accordingly, the specificity and the sensitivity which are advantages of immunoassay are likely to be impaired. In contrast, according to the cyclic peptide according to the embodiment of the present invention, even in a case where a number of the cyclic peptides bind to an antibody, the structural integrity of the antibody can be maintained, and the antibody binding activity is not reduced. Therefore, even in a case where a number of the cyclic peptides bind to an antibody, the detection sensitivity could be improved without impairing the specificity and the sensitivity which are advantages of immunoassay. In addition, because the cyclic peptide binds to an antibody through an antigen-antibody reaction, the separation of the cyclic peptide after labeling that was difficult to perform in the related art can be conducted, and hence reversible labeling can be realized.

The bond between the cyclic peptide according to the embodiment of the present invention and an antibody may be formed by cross-linking the side-chain functional group of the amino acid residue constituting the cyclic peptide according to the embodiment of the present invention and the side-chain functional group of the amino acid residue constituting the antibody by using a cross-linking agent.

Examples of the cross-linking agent include an amino group-amino group cross-linking agent, an amino group-thiol group cross-linking agent, a carboxy group-amino group cross-linking agent, a thiol group-thiol group cross-linking agent, and the like.

Examples of the amino group-amino group cross-linking agent include disuccinimidyl glutarate (DSG), disuccinimidyl suberate (DSS), bis(sulfosuccinimidyl)suberate (BS3), dimethyl adipimidate (DMA), dimethyl pimelimidate (DMP), dimethyl pimelimidate (DMS), and the like.

Examples of the amino group-thiol group cross-linking agent include succinimidyl iodoacetate (SIA), succinimidyl-3-(bromoacetamido)propionate (SBAP), succinimidyl(4-iodoacetyl)aminobenzoate (SIAB), N-α-maleimidoacet-oxysuccinimide ester (AMAS), N-β-maleimidopropyl-oxysuccinimide ester (BMPS), N-γ-maleimidobutyl-oxysuccinimide ester (GMBS), succinimidyl-3-(2-pyridyldithio)propionate (SPDP), succinimidyl-6-(3(2-pyridyldithio)propionamide)hexanoate (LC-SPDP), 4-succinimidyloxycarbonyl-α-methyl-α-(2-pyridyldithio)toluene (SMPT), and the like.

Examples of the carboxy group-amino group cross-linking agent include 1-ethyl-3-(3-dimethylaminopropyl)carbodiimide hydrochloride (EDC), N-hydroxysuccinimide (NHS), sulfo-N-hydroxysulfosuccinimide (Sulfo-NHS), and the like.

Examples of the thiol group-thiol group cross-linking agent include bismaleimidoethane (BMOE), 1,4-bismaleimidobutane (BMB), bismaleimidohexane (BMH), and the like.

Furthermore, the bond between the cyclic peptide according to the embodiment of the present invention and an antibody may be formed by a chemical conjugation by affinity peptide (CCAP) method (see WO2016/186206A).

The CCAP method is a method in which a group having a functional group (referred to as "reactive functional group"), which can react with a functional group such as a side-chain amino group or a side-chain thiol group of an antibody, is introduced into a functional group such as a side-chain amino group or a side-chain thiol group of the cyclic peptide according to the embodiment of the present invention; first the cyclic peptide according to the embodiment of the present invention and the antibody are bonded to each other by an antigen-antibody reaction; and then the reactive functional group introduced into the cyclic peptide is coupled with the functional group such as the amino group or the thiol group of the antibody such that a covalent bond is formed.

Examples of the reactive functional group include an NHS ester group and an imide ester group which can react with an amino group, a maleimide group and a haloacetyl group which can react with a thiol group, and the like.

In the CCAP method, the reaction rapidly and quantitatively proceeds under the weakly acidic to neutral conditions. Therefore, the stability and the affinity of the cyclic peptide according to the embodiment of the present invention, the antibody, and the label are not impaired.

For example, through the reaction illustrated below, by bonding a group having an NHS-ester group to the side-chain amino group of the amino acid residue constituting the cyclic peptide according to the embodiment of the present invention and coupling the NHS-ester group with an amino group of an antibody, a covalent bond can be formed.

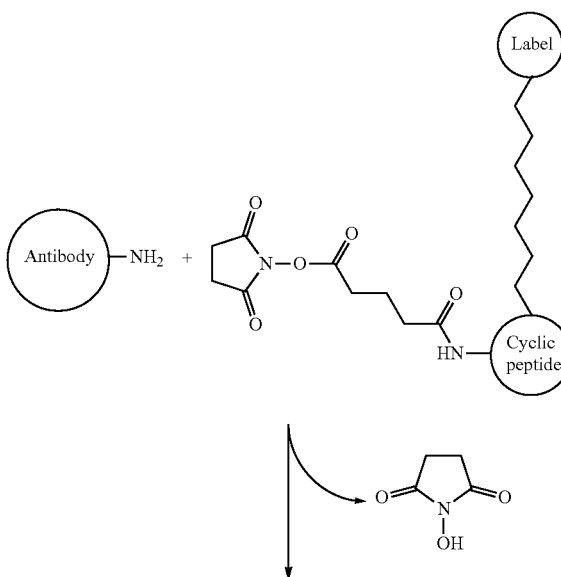

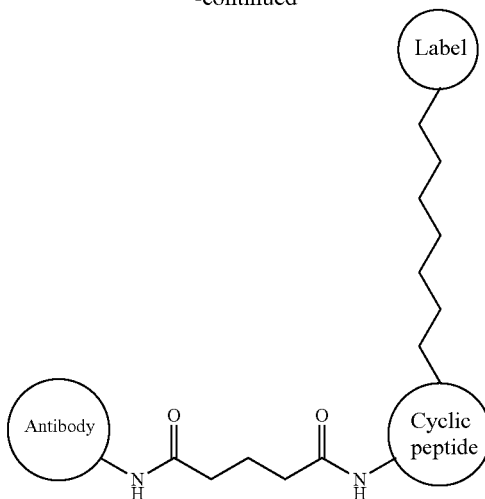

<Linker for Antibody Drug Conjugates and Antibody Drug Conjugate>

In the technical field of antibody drug conjugates, the cyclic peptide according to the embodiment of the present invention can be used as a linker for antibody drug conjugates.

Examples of applications of the cyclic peptide according to the embodiment of the present invention used as a linker for antibody drug conjugates include an antibody drug conjugate which includes an antibody, a drug, and the cyclic peptide according to the embodiment of the present invention and in which the antibody binds to the drug through the cyclic peptide according to the embodiment of the present invention The antibody drug conjugate (ADC) is also called by another name "armed antibody". ADC is a drug obtained by binding an antibody recognizing a cell to a drug (low-molecular weight drug) which is a main active component by using an appropriate linker. The mechanism of action of the antibody drug conjugate is roughly as below.

(1) The antibody portion of an antibody drug conjugate binds to a target molecule on the surface of a target cell.

(2) The antibody drug conjugate infiltrates into the cell.

(3) The linker of the antibody drug conjugate is cleaved in the cell.

(4) The drug (low-molecular weight drug) exerts its efficacy in the cell.

With the antibody drug conjugate, because the efficacy is exerted only in the cell expressing a molecule that the antibody targets, it is possible to inhibit the systemic side effects and to cause the efficacy to be exerted mainly in a target cell. Therefore, the antibody drug conjugate is more efficacious and causes less side effects compared to simple drugs. For example, the anticancer agent developed for attacking cancer cells in which cell division vigorously occurs also attacks the cells, in which cell division vigorously occurs as in the cancer cells but the function thereof is maintained, specifically, the cells responsible for immunity, the cells of the gastrointestinal tract, the hair follicle cells, and the like. Consequently, as side effects, the symptoms such as vulnerability to infectious diseases, diarrhea, and hair loss occur in some cases. However, with the antibody drug conjugate, the anticancer agent can be selectively carried to target cancer cells, and accordingly, it is possible to inhibit the side effects caused in a case where the anticancer agent attacks cells other than the target cells.

A linker for antibody drug conjugates is required to link the antibody portion of the antibody drug conjugates to the drug portion, be stable in the blood, and cut off the drug from the antibody in a cell such that the drug is released. Furthermore, the linker for antibody drug conjugates is also required not to impair the binding activity of the antibody. In order to improve the drug carrying efficiency, a number of drugs need to be attached to one antibody molecule. However, with the linker for antibody drug conjugates of the related art, in a case where a number of the linkers bind to an antibody, the antibody binding activity deteriorates. As a result, the selectivity which is the advantage of an antibody drug conjugate is impaired, and the drug is likely to be carried to target cells with low efficiency. However, with the cyclic peptide according to the embodiment of the present invention, even in a case where a number of the cyclic peptides bind to an antibody, the structural integrity of the antibody can be maintained, and the antibody binding activity is not reduced. Accordingly, even in a case where a number of the cyclic peptides bind to an antibody, the selectivity which is the advantage of an antibody drug conjugate is not impaired, and the drug could be carried to target cells with improved efficiency.

Furthermore, because the temporal stability of the cyclic peptide according to the embodiment of the present invention is higher than that of the cyclic peptide of the related art, it is expected that the stability of the linker for antibody drug conjugates and the antibody drug conjugates in the blood will be improved.

In addition, it is expected that by modifying the side-chain portion of a triazole bond which is a cyclic portion, the drug releasing properties in a cell will be controlled.

The bond between the cyclic peptide according to the embodiment of the present invention and an antibody may be formed by cross-linking the side-chain functional group of the amino acid residue constituting the cyclic peptide according to the embodiment of the present invention and the side-chain functional group of the amino acid residue constituting the antibody by using a cross-linking agent.

Examples of the cross-linking agent include an amino group-amino group cross-linking agent, an amino group-thiol group cross-linking agent, a carboxy group-amino group cross-linking agent, a thiol group-thiol group cross-linking agent, and the like.

Examples of the amino group-amino group cross-linking agent include disuccinimidyl glutarate (DSG), disuccinimidyl suberate (DSS), bis(sulfosuccinimidyl)suberate (BS3), dimethyl adipimidate (DMA), dimethyl pimelimidate (DMP), dimethyl pimelimidate (DMS), and the like.

Examples of the amino group-thiol group cross-linking agent include succinimidyl iodoacetate (SIA), succinimidyl-3-(bromoacetamido)propionate (SBAP), succinimidyl(4-iodoacetyl)aminobenzoate (SIAB), N-α-maleimidoacet-oxysuccinimide ester (AMAS), N-β-maleimidopropyl-oxysuccinimide ester (BMPS), N-γ-maleimidobutyl-oxysuccinimide ester (GMBS), succinimidyl-3-(2-pyridyldithio)propionate (SPDP), succinimidyl-6-(3 (2-pyridyldithio)propionamide)hexanoate (LC-SPDP), 4-succinimidyloxycarbonyl-α-methyl-α-(2-pyridyldithio) toluene (SMPT), and the like.

Examples of the carboxy group-amino group cross-linking agent include 1-ethyl-3-(3-dimethylaminopropyl)carbodiimide hydrochloride (EDC), N-hydroxysuccinimide (NHS), sulfo-N-hydroxysulfosuccinimide (Sulfo-NHS), and the like.

Examples of the thiol group-thiol group cross-linking agent include bismaleimidoethane (BMOE), 1,4-bismaleimidobutane (BMB), bismaleimidohexane (BMH), and the like.

Furthermore, the bond between the cyclic peptide according to the embodiment of the present invention and an antibody may be formed by a chemical conjugation by affinity peptide (CCAP) method (see WO2016/186206A).

The CCAP method is a method in which a group having a functional group (referred to as "reactive functional group"), which can react with a functional group such as a side-chain amino group or a side-chain thiol group of an antibody, is introduced into a functional group such as a side-chain amino group or a side-chain thiol group of the cyclic peptide according to the embodiment of the present invention; first the cyclic peptide according to the embodiment of the present invention and the antibody are bonded to each other by an antigen-antibody reaction; and then the reactive functional group introduced into the cyclic peptide is coupled with the functional group such as the amino group or the thiol group of the antibody such that a covalent bond is formed.

Examples of the reactive functional group include an NHS-ester group and an imide ester group which can react with an amino group, a maleimide group and a haloacetyl group which can react with a thiol group, and the like.

In the CCAP method, the reaction rapidly and quantitatively proceeds under the weakly acidic to neutral conditions. Therefore, the stability and the affinity of the cyclic peptide according to the embodiment of the present invention, the antibody, and the drug are not impaired.

For example, through the reaction illustrated below, by bonding a group having a maleimide group to the side-chain amino group of the amino acid residue constituting the cyclic peptide according to the embodiment of the present invention and coupling the maleimide group with a thiol group of an antibody, a covalent bond can be formed.

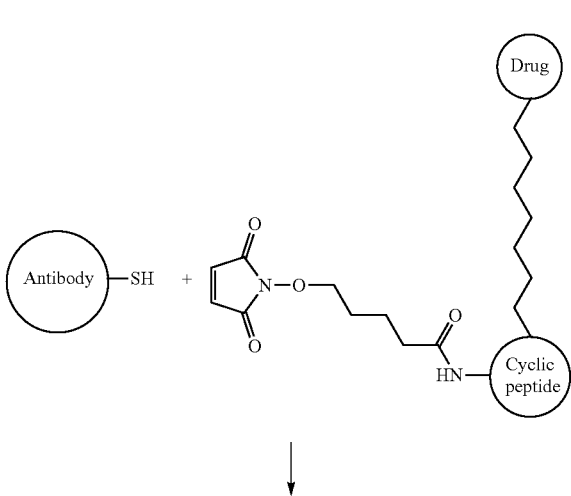

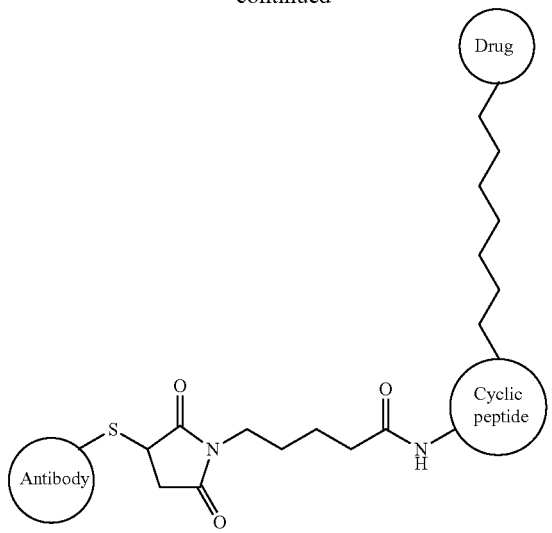

The drug may be a liposomized drug, a polymerically micellized drug, or a polyethylene glycolated (PEGylated) drug.

By liposomizing, polymerically micellizing, or PEGylating the drug, in many cases, it is possible to improve the in vivo stability of active components, the pharmacokinetics including a tissue migration profile, the intracellular pharmacokinetics, and the like.

<Drug Carrier and Pharmaceutical Preparation>

The cyclic peptide according to the embodiment of the present invention can be used as a drug carrier in a drug delivery system.

Examples of applications of the cyclic peptide according to the embodiment of the present invention used as a drug carrier include a pharmaceutical preparation which includes a drug and the cyclic peptide according to the embodiment of the present invention and in which the drug and the cyclic peptide according to the embodiment of the present invention are directly or indirectly bonded to each other.

In a case where the cyclic peptide according to the embodiment of the present invention binds to IgG present in a biological body, the same effects as those brought about by the aforementioned antibody drug conjugate could be obtained. The drug may bind to the cyclic peptide as it is or bind to the cyclic peptide as a drug having undergone liposomization, polymer micellization, or polyethylene glycolation (PEGylation). Furthermore, the drug may bind to the cyclic peptide through polysaccharides such as dextran or a hydrophilic polymer.

EXAMPLES

Hereinafter, the present invention will be more specifically described based on examples, but the present invention is not limited to the examples.

Example 1

(1) Synthesis of Cyclic Peptide

A cyclic polypeptide (SEQ ID NO: 3) represented by Formula (3) was synthesized using a full automatic peptide synthesis device (PSSM-8, manufactured by Shimadzu Corporation). Hereinafter, this cyclic peptide will be referred to as "cyclic peptide 1" in some cases.

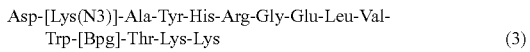

Asp-[Lys(N3)]-Ala-Tyr-His-Arg-Gly-Glu-Leu-Val-Trp-[Bpg]-Thr-Lys-Lys  (3)

In Formula (3), [Lys(N3)] represents an amino acid residue derived from ε-azide-L-lysine, [Bpg] represents an amino acid residue derived from L-bishomopropargylglycine, and [Lys(N3)] and [Bpg] are cross-linked to each other through a triazole bond formed by a cycloaddition reaction between a side-chain azide group and a side-chain ethynyl group (see the following chemical formula).

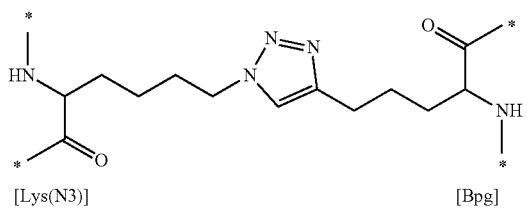

In the above chemical formula, "*" represents a point of binding to an adjacent amino acid residue.

(2) Ligand Immobilization

A commercially available CM5 (carboxymethyl dextran introduction-type, manufactured by GE Healthcare) sensor chip was set in Biacore 3000 (Biacore is a registered trademark) as a surface plasmon resonance device manufactured by GE Healthcare, a 4-(2-hydroxyethyl)-1-piperazineethanesulfonic acid (HEPES) buffer solution (20 mM HEPES-HCl, 150 mM NaCl, pH 7.4) for surface plasmon resonance (SPR) was stabilized at a flow rate of 10 µL/min, and 70 µL of an aqueous mixed solution of 0.2 M 1-(3-Dimethylaminopropyl)-3-ethylcarbodiimide (EDC) and 0.04 µM of N-Hydroxysuccinimide (NHS) were injected thereinto. Thereafter, 100 µL of a sample solution of the cyclic peptide 1, which was diluted with a HEPES buffer solution at 0.2 g/L and treated with a polytetrafluoroethylene (PTFE) filter (manufactured by Advantec MFS, Inc.) having a diameter of 0.20 µm, was supplied to the sensor chip. Then, a blocking treatment was then performed on the sample solution by using an aqueous ethanolamine solution, and the sensor chip was washed with an aqueous sodium hydroxide solution, thereby performing immobilization. Likewise, 70 µL of an aqueous mixed solution of 0.2 M EDC and 0.04 M NHS was added to the same sensor chip without immobilizing the sample in another flow channel of the sensor chip, and then the blocking treatment and the washing treatment were performed. Hereinafter, the obtained immobilized sensor chip will be referred to as "immobilized sensor chip A".

(3) Evaluation of Binding Activity

At 25° C., 3,000 nM of human immunoglobulin G (IgG) antibodies were added for 10 minutes to the immobilized sensor chip A prepared in (2) described above. Then, the antibody binding amount in the flow channel in which the cyclic peptide was immobilized immediately after the addition and in the flow channel in which the cyclic peptide was not immobilized was measured. From the difference in the antibody binding amount between the flow channel in which the cyclic peptide was immobilized and the flow channel in which the cyclic peptide was not immobilized and the amount of the immobilized cyclic peptide, the activity of the cyclic peptide was calculated. Furthermore, by regarding the activity of a cyclic peptide 5 in Comparative Example 1 as 1, the relative binding activity with respect to the human IgG antibodies was calculated.

(Evaluation Standards for Relative Binding Activity)

The relative binding activity was higher than 800% of the binding activity of the cyclic peptide 5. . . . A The relative binding activity was higher than 400% and equal to or lower than 800% of the binding activity of the cyclic peptide 5. . . . B The relative binding activity was higher than 200% and equal to or lower than 400% of the binding activity of the cyclic peptide 5. . . . C The relative binding activity was higher than 100% and equal to or lower than 200% of the binding activity of the cyclic peptide 5. . . . D The relative binding activity was equal to or lower than 100% of the binding activity of the cyclic peptide 5. . . . E The evaluation results are shown in the column of "Relative binding activity" in Table 3.

The grades A, B, and C show that the immobilization brings about a sufficient improving effect, and the grades D and E show that sufficient binding activity is not exhibited.

In a case where a cyclic peptide exhibiting sufficient binding activity is used, the cyclic peptide can specifically bind to antibodies, antibodies can be more efficiently purified, and the antibody purification cost can be further reduced.

(4) Ligand Immobilization 1 mL of HiTrap NHS-activated HP Columns (coupling columns for ligand immobilization, manufactured by GE Healthcare) (HITRAP is a registered trademark) was reacted with 1 mL of 10 mg/mL cyclic peptide solution, which was prepared by dissolving the cyclic peptide 1 in an immobilization buffer (10% DMSO in 200 mM NaHCO$_3$, 500 mM NaCl, pH 8.3), for 1 hour at 25° C. The reaction product was blocked by an aqueous ethanolamine solution and washed, thereby obtaining a cyclic peptide 1-immobilized support. Hereinafter, the obtained immobilized support will be referred to as "immobilized support A".

(5) Evaluation of Chemical Resistance

The immobilized support A prepared in (4) described above was connected to a chromatography system AKTA avant 25 (manufactured by GE Healthcare) (AKTAAVANT is a registered trademark), and the antibody binding amount was measured. The columns were equilibrated using an equilibration solution (20 mM phosphoric acid buffer, 150 mM NaCl, pH 7.4), and then 20 mL of a 5 mg/mL human IgG antibody standard buffer solution (20 mM phosphoric acid buffer, 150 mM NaCl, pH 7.4) was injected thereinto at a flow rate of 0.21 mL/min. Thereafter, the columns were washed with 5 mL of a postloading wash solution (20 mM phosphoric acid buffer, 150 mM NaCl, pH 7.4) caused to flow at the same flow rate and then washed with 5 mL of a pre-elution wash solution (20 mM phosphoric acid buffer, 1 M NaCl, pH 7.4) at the same flow rate. Then, 5 mL of an elution solution (100 mM citric acid buffer, pH 3.2) was caused to flow at the same flow rate. Subsequently, 5 mL of a cleaning in place (CIP) solution (0.1 M sodium hydroxide) was caused to flow at the same flow rate, and then 5 mL of a reequilibration solution (20 mM phosphoric acid buffer, 150 mM NaCl, pH 7.4) was caused to flow at the same flow rate. At this time, by using an immunoglobulin G (IgG) elution peak obtained by monitoring absorbance at 280 nm, the amount of antibodies binding to the support until 10% of the antibody stock solution leaked out of the support was measured as the antibody binding amount. Then, the immobilized support A was filled with a 0.05 M aqueous NaOH solution for 6 hours at 25° C. and left to stand, the antibody binding amount of the support was then measured in the same manner, and a rate of change in the binding amount was calculated from the antibody binding amount before and after the alkali treatment.

(Evaluation Standards of Rate of Change in Binding Amount)

The rate of change in the binding amount was higher than 90% . . . A

The rate of change in the binding amount was higher than 80% and equal to or lower than 90% . . . B The rate of change in the binding amount was higher than 70% and equal to or lower than 80% . . . C The rate of change in the binding amount was higher than 50% and equal to or lower than 70% . . . D The rate of change in the binding amount was equal to or lower than 50% . . . E The evaluation results are shown in the column of "Chemical resistance" in Table 3.

The grades A, B, and C show that the chemical resistance is sufficient, and the grades D and E show that sufficient chemical resistance is not exhibited. In a case where a cyclic peptide exhibiting sufficient chemical resistance is used, the cyclic peptide can repeatedly specifically bind to antibodies even after washing, antibodies can be purified for a long period of time, and the antibody purification costs can be reduced.

(6) Evaluation of Stability in Human Plasma

The stability of the cyclic peptide 1 in human plasma (manufactured by ProMedDX) was evaluated.

A 5 µM aqueous solution of the cyclic peptide 1 was prepared, and 2 µL of the aqueous solution was added to 20 µL of the human plasma and left to stand for 20 minutes at room temperature. After 20 minutes, 100 µL of methanol (manufactured by Wako Pure Chemical Industries, Ltd.) was added thereto such that the reaction stopped. After being stirred, the solution was subjected to centrifugation, and the supernatant was collected and named 20-minute sample. Meanwhile, 100 µL of methanol was added to 20 µL of the human plasma, 2 µL of the aqueous solution of the cyclic peptide was then added thereto, the solution was stirred and subjected to centrifugation, and the supernatant was collected. The collected supernatant was named 0-minute sample.

By using a mass spectrometer TRIPLE QUAD 5500 (manufactured by AB Sciex Pte. Ltd.), the content of the cyclic peptide 1 in each of the 0-minute sample and the 20-minute sample was quantified. By regarding the quantified value obtained from the 0-minute sample as 100%, the quantified value obtained from the 20-minute sample was calculated as a residual rate.

(Evaluation Standards for Residual Rate)

The rate of change in the binding amount was higher than 90% . . . A

The rate of change in the binding amount was higher than 80% and equal to or lower than 90% . . . B The rate of change in the binding amount was higher than 70% and equal to or lower than 80% . . . C The rate of change in the binding amount was higher than 50% and equal to or lower than 70% . . . D The rate of change in the binding amount was equal to or lower than 50% . . . E The structures of the cyclic peptides and the evaluation results are shown in the column of "Stability in plasma" in Table 3.

Example 2

(1) Based on Example 1, a cyclic peptide (SEQ ID NO: 4) represented by Formula (4) was synthesized. Hereinafter, this cyclic peptide will be referred to as "cyclic peptide 2" in some cases.

Asp-[Lys(N3)]-Ala-Tyr-His-Leu-Gly-Glu-Leu-Val-Trp-[Bpg]-Thr-Lys-Lys   (4)

In Formula (4), [Lys(N3)] represents an amino acid residue derived from ε-azide-L-lysine, [Bpg] represents an amino acid residue derived from L-bishomopropargylglycine, and [Lys(N3)] and [Bpg] are cross-linked to each other through a triazole bond formed by a cycloaddition reaction between a side-chain azide group and a side-chain ethynyl group (see the following chemical formula).

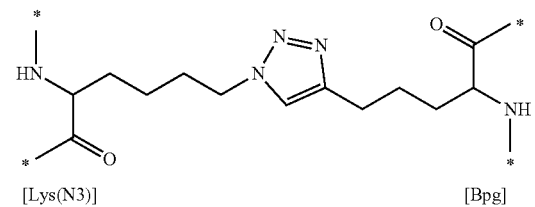 [SMILES: CNC(CCCCn1cc(CCCC(NC)C(C)=O)nn1)C(C)=O]

[Lys(N3)]                                        [Bpg]

In the above chemical formula, "*" represents a point of binding to an adjacent amino acid residue.

(2) An immobilized sensor chip B was obtained in the same manner as in Example 1, except that the cyclic peptide 2 was used instead of the cyclic peptide 1.

(3) The binding activity was evaluated in the same manner as in Example 1. The evaluation results are shown in the column of "Relative binding activity" in Table 3.

(4) An immobilized support B was obtained in the same manner as in Example 1, except that the cyclic peptide 2 was used instead of the cyclic peptide 1.

(5) The chemical resistance was evaluated in the same manner as in Example 1. The evaluation results are shown in the column of "Chemical resistance" in Table 3.

(6) The stability of the cyclic peptide 2 in the human plasma was evaluated in the same manner as in Example 1. The evaluation results are shown in the column of "Stability in plasma" in Table 3.

Example 3

(1) Based on Example 1, a cyclic peptide (SEQ ID NO: 5) represented by Formula (5) was synthesized. Hereinafter, this cyclic peptide will be referred to as "cyclic peptide 3" in some cases.

Asp-[Bpg]-Ala-Tyr-His-Leu-Gly-Glu-Leu-Val-Trp-[Lys(N3)]-Thr-Lys-Lys   (5)

In Formula (5), [Bpg] represents an amino acid residue derived from L-bishomopropargylglycine, [Lys(N3)] represents an amino acid residue derived from ε-azide-L-lysine, and [Bpg] and [Lys(N3)] are cross-linked to each other through a triazole bond formed by a cycloaddition reaction between a side-chain ethynyl group and a side-chain azide group.

(2) An immobilized sensor chip C was obtained in the same manner as in Example 1, except that the cyclic peptide 3 was used instead of the cyclic peptide 1.

(3) The binding activity was evaluated in the same manner as in Example 1. The evaluation results are shown in the column of "Relative binding activity" in Table 3.

(4) An immobilized support C was obtained in the same manner as in Example 1, except that the cyclic peptide 3 was used instead of the cyclic peptide 1.

(5) The chemical resistance was evaluated in the same manner as in Example 1. The evaluation results are shown in the column of "Chemical resistance" in Table 3.

Example 4

(1) Based on Example 1, a cyclic peptide (SEQ ID NO: 6) represented by Formula (6) was synthesized. Hereinafter, this cyclic peptide will be referred to as "cyclic peptide 4" in some cases.

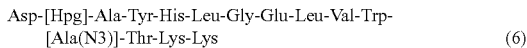

Asp-[Hpg]-Ala-Tyr-His-Leu-Gly-Glu-Leu-Val-Trp-
[Ala(N3)]-Thr-Lys-Lys    (6)

In Formula (6), [Hpg] represents an amino acid residue derived from L-homopropargylglycine, [Ala(N3)] represents an amino acid residue derived from β-azide-L-alanine, and [Hpg] and [Ala(N3)] are cross-linked to each other through a triazole bond formed by a cycloaddition reaction between a side-chain ethynyl group and a side-chain azide group (see the following chemical formula).

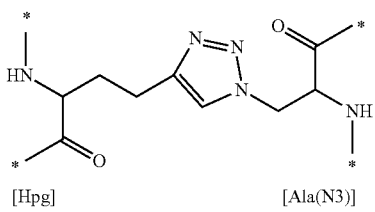 [SMILES: CNC(CCc1cn(CC(NC)C(C)=O)nn1)C(C)=O]

[Hpg]                    [Ala(N3)]

In the above chemical formula, "*" represents a point of binding to an adjacent amino acid residue.

(2) An immobilized sensor chip D was obtained in the same manner as in Example 1, except that the cyclic peptide 4 was used instead of the cyclic peptide 1.

(3) The binding activity was evaluated in the same manner as in Example 1. The evaluation results are shown in the column of "Relative binding activity" in Table 3.

(4) An immobilized support D was obtained in the same manner as in Example 1, except that the cyclic peptide 4 was used instead of the cyclic peptide 1.

(5) The chemical resistance was evaluated in the same manner as in Example 1. The evaluation results are shown in the column of "Chemical resistance" in Table 3.

(6) The stability of the cyclic peptide 4 in the human plasma was evaluated in the same manner as in Example 1. The evaluation results are shown in the column of "Stability in plasma" in Table 3.

Example 5

(1) Based on Example 1, a cyclic peptide (SEQ ID NO: 7) represented by Formula (7) was synthesized. Hereinafter, this cyclic peptide will be referred to as "cyclic peptide 5" in some cases.

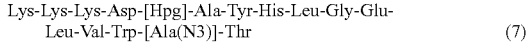

Lys-Lys-Lys-Asp-[Hpg]-Ala-Tyr-His-Leu-Gly-Glu-
Leu-Val-Trp-[Ala(N3)]-Thr    (7)

In Formula (7), [Hpg] represents an amino acid residue derived from L-homopropargylglycine, [Ala(N3)] represents an amino acid residue derived from β-azide-L-alanine, and [Hpg] and [Ala(N3)] are cross-linked to each other through a triazole bond formed by a cycloaddition reaction between a side-chain ethynyl group and a side-chain azide group.

(2) An immobilized sensor chip E was obtained in the same manner as in Example 1, except that the cyclic peptide 5 was used instead of the cyclic peptide 1.

(3) The binding activity was evaluated in the same manner as in Example 1. The evaluation results are shown in the column of "Relative binding activity" in Table 3.

(4) An immobilized support E was obtained in the same manner as in Example 1, except that the cyclic peptide 5 was used instead of the cyclic peptide 1.

(5) The chemical resistance was evaluated in the same manner as in Example 1. The evaluation results are shown in the column of "Chemical resistance" in Table 3.

Example 6

(1) Based on Example 1, a cyclic peptide (SEQ ID NO: 8) represented by Formula (8) was synthesized. Hereinafter, this cyclic peptide will be referred to as "cyclic peptide 6" in some cases.

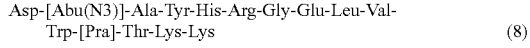

Asp-[Abu(N3)]-Ala-Tyr-His-Arg-Gly-Glu-Leu-Val-
Trp-[Pra]-Thr-Lys-Lys    (8)

In Formula (8), [Abu(N3)] represents an amino acid residue derived from γ-azide-L-homoalanine, [Pra] represents an amino acid residue derived from L-homopropargylglycine, and [Abu(N3)] and [Pra] are cross-linked to each other through a triazole bond formed by a cycloaddition reaction between a side-chain azide group and a side-chain ethynyl group.

(2) An immobilized sensor chip F was obtained in the same manner as in Example 1, except that the cyclic peptide 6 was used instead of the cyclic peptide 1.

(3) The binding activity was evaluated in the same manner as in Example 1. The evaluation results are shown in the column of "Relative binding activity" in Table 3.

(4) An immobilized support F was obtained in the same manner as in Example 1, except that the cyclic peptide 6 was used instead of the cyclic peptide 1.

(5) The chemical resistance was evaluated in the same manner as in Example 1. The evaluation results are shown in the column of "Chemical resistance" in Table 3.

Example 7

(1) Based on Example 1, a cyclic peptide (SEQ ID NO: 9) represented by Formula (9) was synthesized. Hereinafter, this cyclic peptide will be referred to as "cyclic peptide 7" in some cases.

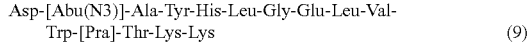

Asp-[Abu(N3)]-Ala-Tyr-His-Leu-Gly-Glu-Leu-Val-
Trp-[Pra]-Thr-Lys-Lys    (9)

In Formula (9), [Abu(N3)] represents an amino acid residue derived from γ-azide-L-homoalanine, [Pra] represents an amino acid residue derived from L-propargylglycine, and [Abu(N3)] and [Pra] are cross-linked to each other through a triazole bond formed by a cycloaddition reaction between a side-chain azide group and a side-chain ethynyl group.

(2) An immobilized sensor chip G was obtained in the same manner as in Example 1, except that the cyclic peptide 7 was used instead of the cyclic peptide 1.

(3) The binding activity was evaluated in the same manner as in Example 1. The evaluation results are shown in the column of "Relative binding activity" in Table 3.

(4) An immobilized support G was obtained in the same manner as in Example 1, except that the cyclic peptide 7 was used instead of the cyclic peptide 1.

(5) The chemical resistance was evaluated in the same manner as in Example 1. The evaluation results are shown in the column of "Chemical resistance" in Table 3.

Example 8

(1) Based on Example 1, a cyclic peptide (SEQ ID NO: 10) represented by Formula (10) was synthesized. Hereinafter, this cyclic peptide will be referred to as "cyclic peptide 8" in some cases.

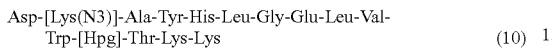
Asp-[Lys(N3)]-Ala-Tyr-His-Leu-Gly-Glu-Leu-Val-Trp-[Hpg]-Thr-Lys-Lys  (10)

In Formula (10), [Lys(N3)] represents an amino acid residue derived from ε-azide-L-lysine, [Hpg] represents an amino acid residue derived from L-homopropargylglycine, and [Lys(N3)] and [Hpg] are cross-linked to each other through a triazole bond formed by a cycloaddition reaction between a side-chain azide group and a side-chain ethynyl group.

(2) An immobilized sensor chip H was obtained in the same manner as in Example 1, except that the cyclic peptide 8 was used instead of the cyclic peptide 1.

(3) The binding activity was evaluated in the same manner as in Example 1. The evaluation results are shown in the column of "Relative binding activity" in Table 3.

(4) An immobilized support H was obtained in the same manner as in Example 1, except that the cyclic peptide 8 was used instead of the cyclic peptide 1.

(5) The chemical resistance was evaluated in the same manner as in Example 1. The evaluation results are shown in the column of "Chemical resistance" in Table 3.

Example 9

(1) Based on Example 1, a cyclic peptide (SEQ ID NO: 11) represented by Formula (11) was synthesized. Hereinafter, this cyclic peptide will be referred to as "cyclic peptide 9" in some cases.

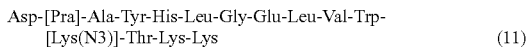
Asp-[Pra]-Ala-Tyr-His-Leu-Gly-Glu-Leu-Val-Trp-[Lys(N3)]-Thr-Lys-Lys  (11)

In Formula (11), [Pra] represents an amino acid residue derived from L-propargylglycine, [Lys(N3)] represents an amino acid residue derived from ε-azide-L-lysine, and [Pra] and [Lys(N3)] are cross-linked to each other through a triazole bond formed by a cycloaddition reaction between a side-chain ethynyl group and a side-chain azide group.

(2) An immobilized sensor chip I was obtained in the same manner as in Example 1, except that the cyclic peptide 9 was used instead of the cyclic peptide 1.

(3) The binding activity was evaluated in the same manner as in Example 1. The evaluation results are shown in the column of "Relative binding activity" in Table 3.

(4) An immobilized support I was obtained in the same manner as in Example 1, except that the cyclic peptide 9 was used instead of the cyclic peptide 1.

(5) The chemical resistance was evaluated in the same manner as in Example 1. The evaluation results are shown in the column of "Chemical resistance" in Table 3.

Example 10

(1) Based on Example 1, a cyclic peptide (SEQ ID NO: 12) represented by Formula (12) was synthesized. Hereinafter, this cyclic peptide will be referred to as "cyclic peptide 10" in some cases.

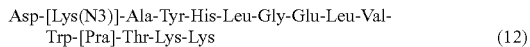
Asp-[Lys(N3)]-Ala-Tyr-His-Leu-Gly-Glu-Leu-Val-Trp-[Pra]-Thr-Lys-Lys  (12)

In Formula (12), [Lys(N3)] represents an amino acid residue derived from ε-azide-L-lysine, [Pra] represents an amino acid residue derived from L-propargylglycine, and [Lys(N3)] and [Pra] are cross-linked to each other through a triazole bond formed by a cycloaddition reaction between a side-chain azide group and a side-chain ethynyl group.

(2) An immobilized sensor chip J was obtained in the same manner as in Example 1, except that the cyclic peptide 10 was used instead of the cyclic peptide 1.

(3) The binding activity was evaluated in the same manner as in Example 1. The evaluation results are shown in the column of "Relative binding activity" in Table 3.

(4) An immobilized support J was obtained in the same manner as in Example 1, except that the cyclic peptide 10 was used instead of the cyclic peptide 1.

(5) The chemical resistance was evaluated in the same manner as in Example 1. The evaluation results are shown in the column of "Chemical resistance" in Table 3.

Example 11

(1) Based on Example 1, a cyclic peptide (SEQ ID NO: 13) represented by Formula (13) was synthesized. Hereinafter, this cyclic peptide will be referred to as "cyclic peptide 11" in some cases.

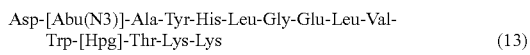
Asp-[Abu(N3)]-Ala-Tyr-His-Leu-Gly-Glu-Leu-Val-Trp-[Hpg]-Thr-Lys-Lys  (13)

In Formula (13), [Abu(N3)] represents an amino acid residue derived from γ-azide-L-homoalanine, [Hpg] represents an amino acid residue derived from L-homopropargylglycine, and [Abu(N3)] and [Hpg] are cross-linked to each other through a triazole bond formed by a cycloaddition reaction between a side-chain azide group and a side-chain ethynyl group.

(2) An immobilized sensor chip K was obtained in the same manner as in Example 1, except that the cyclic peptide 11 was used instead of the cyclic peptide 1.

(3) The binding activity was evaluated in the same manner as in Example 1. The evaluation results are shown in the column of "Relative binding activity" in Table 3.

(4) An immobilized support K was obtained in the same manner as in Example 1, except that the cyclic peptide 11 was used instead of the cyclic peptide 1.

(5) The chemical resistance was evaluated in the same manner as in Example 1. The evaluation results are shown in the column of "Chemical resistance" in Table 3.

Example 12

(1) Based on Example 1, a cyclic peptide (SEQ ID NO: 14) represented by Formula (14) was synthesized. Hereinafter, this cyclic peptide will be referred to as "cyclic peptide 12" in some cases.

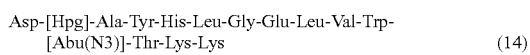
Asp-[Hpg]-Ala-Tyr-His-Leu-Gly-Glu-Leu-Val-Trp-[Abu(N3)]-Thr-Lys-Lys  (14)

In Formula (14), [Hpg] represents an amino acid residue derived from L-homopropargylglycine, [Abu(N3)] represents an amino acid residue derived from γ-azide-L-homoalanine, and [Hpg] and [Abu(N3)] are cross-linked to each other through a triazole bond formed by a cycloaddition reaction between a side-chain ethynyl group and a side-chain azide group.

(2) An immobilized sensor chip L was obtained in the same manner as in Example 1, except that the cyclic peptide 12 was used instead of the cyclic peptide 1.

(3) The binding activity was evaluated in the same manner as in Example 1. The evaluation results are shown in the column of "Relative binding activity" in Table 3.

(4) An immobilized support L was obtained in the same manner as in Example 1, except that the cyclic peptide 12 was used instead of the cyclic peptide 1.

(5) The chemical resistance was evaluated in the same manner as in Example 1. The evaluation results are shown in the column of "Chemical resistance" in Table 3.

Example 13

(1) Based on Example 1, a cyclic peptide (SEQ ID NO: 15) represented by Formula (15) was synthesized. Hereinafter, this cyclic peptide will be referred to as "cyclic peptide 13" in some cases.

Asp-[Abu(N3)]-Ala-Tyr-His-Leu-Gly-Glu-Leu-Val-Trp-[Bpg]-Thr-Lys-Lys    (15)

In Formula (15), [Abu(N3)] represents an amino acid residue derived from γ-azide-L-homoalanine, [Bpg] represents an amino acid residue derived from L-bishomopropargylglycine, and [Abu(N3)] and [Bpg] are cross-linked to each other through a triazole bond formed by a cycloaddition reaction between a side-chain azide group and a side-chain ethynyl group.

(2) An immobilized sensor chip M was obtained in the same manner as in Example 1, except that the cyclic peptide 13 was used instead of the cyclic peptide 1.

(3) The binding activity was evaluated in the same manner as in Example 1. The evaluation results are shown in the column of "Relative binding activity" in Table 3.

(4) An immobilized support M was obtained in the same manner as in Example 1, except that the cyclic peptide 13 was used instead of the cyclic peptide 1.

(5) The chemical resistance was evaluated in the same manner as in Example 1. The evaluation results are shown in the column of "Chemical resistance" in Table 3.

Example 14

(1) Based on Example 1, a cyclic peptide (SEQ ID NO: 16) represented by Formula (16) was synthesized. Hereinafter, this cyclic peptide will be referred to as "cyclic peptide 14" in some cases.

Asp-[Bpg]-Ala-Tyr-His-Leu-Gly-Glu-Leu-Val-Trp-[Nva(N3)]-Thr-Lys-Lys    (16)

In Formula (16), [Bpg] represents an amino acid residue derived from L-bishomopropargylglycine, [Nva(N3)] represents an amino acid residue derived from δ-azide-L-norvaline, and [Bpg] and [Nva(N3)] are cross-linked to each other through a triazole bond formed by a cycloaddition reaction between a side-chain ethynyl group and a side-chain azide group.

(2) An immobilized sensor chip N was obtained in the same manner as in Example 1, except that the cyclic peptide 14 was used instead of the cyclic peptide 1.

(3) The binding activity was evaluated in the same manner as in Example 1. The evaluation results are shown in the column of "Relative binding activity" in Table 3.

(4) An immobilized support N was obtained in the same manner as in Example 1, except that the cyclic peptide 14 was used instead of the cyclic peptide 1.

(5) The chemical resistance was evaluated in the same manner as in Example 1. The evaluation results are shown in the column of "Chemical resistance" in Table 3.

Example 15

(1) Based on Example 1, a cyclic peptide (SEQ ID NO: 17) represented by Formula (17) was synthesized. Hereinafter, this cyclic peptide will be referred to as "cyclic peptide 15" in some cases.

Asp-[Hpg]-Ala-Tyr-His-Leu-Gly-Glu-Leu-Val-Trp-[Nva(N3)]-Thr-Lys-Lys    (17)

In Formula (17), [Hpg] represents an amino acid residue derived from L-homopropargylglycine, [Nva(N3)] represents an amino acid residue derived from δ-azide-L-norvaline, and [Hpg] and [Nva(N3)] are cross-linked to each other through a triazole bond formed by a cycloaddition reaction between a side-chain ethynyl group and a side-chain azide group.

(2) An immobilized sensor chip P was obtained in the same manner as in Example 1, except that the cyclic peptide 15 was used instead of the cyclic peptide 1.

(3) The binding activity was evaluated in the same manner as in Example 1. The evaluation results are shown in the column of "Relative binding activity" in Table 3.

(4) An immobilized support P was obtained in the same manner as in Example 1, except that the cyclic peptide 15 was used instead of the cyclic peptide 1.

(5) The chemical resistance was evaluated in the same manner as in Example 1. The evaluation results are shown in the column of "Chemical resistance" in Table 3.

Example 16

(1) Based on Example 1, a cyclic peptide (SEQ ID NO: 18) represented by Formula (18) was synthesized. Hereinafter, this cyclic peptide will be referred to as "cyclic peptide 16" in some cases.

Asp-[Nva(N3)]-Ala-Tyr-His-Leu-Gly-Glu-Leu-Val-Trp-[Bpg]-Thr-Lys-Lys    (18)

In Formula (18), [Nva(N3)] represents an amino acid residue derived from δ-azide-L-norvaline, [Bpg] represents an amino acid residue derived from L-bishomopropargylglycine, and [Nva(N3)] and [Bpg] are cross-linked to each other through a triazole bond formed by a cycloaddition reaction between a side-chain azide group and a side-chain ethynyl group.

(2) An immobilized sensor chip Q was obtained in the same manner as in Example 1, except that the cyclic peptide 16 was used instead of the cyclic peptide 1.

(3) The binding activity was evaluated in the same manner as in Example 1. The evaluation results are shown in the column of "Relative binding activity" in Table 3.

(4) An immobilized support Q was obtained in the same manner as in Example 1, except that the cyclic peptide 16 was used instead of the cyclic peptide 1.

(5) The chemical resistance was evaluated in the same manner as in Example 1. The evaluation results are shown in the column of "Chemical resistance" in Table 3.

Comparative Example 1

(1) A cyclic peptide (SEQ ID NO: 19) represented by Formula (19) was synthesized using a full automatic peptide synthesis device (PSSM-8, manufactured by Shimadzu Corporation). Hereinafter, this cyclic peptide will be referred to as "cyclic peptide 17" in some cases.

Asp-[Glu]-Ala-Tyr-His-Arg-Gly-Glu-Leu-Val-Trp-[Lys]-Thr-Lys-Lys (19)

In Formula (19), [Glu] represents an amino acid residue derived from L-glutamic acid, [Lys] represents an amino acid residue derived from L-lysine, and [Glu] and [Lys] are cross-linked to each other through an amide bond formed by dehydrocondensation of a side-chain carboxy group and a side-chain amino group (see the following chemical formula).

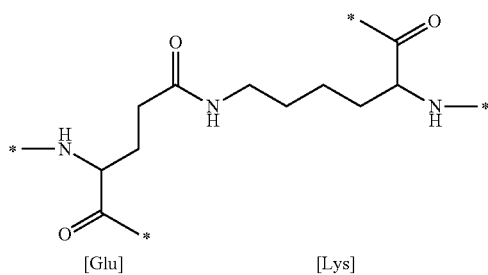

[Glu]    [Lys]

In the above chemical formula, "*" represents a point of binding to an adjacent amino acid residue.

(2) An immobilized sensor chip R was obtained in the same manner as in Example 1, except that the cyclic peptide 17 was used instead of the cyclic peptide 1.

(3) The binding activity was evaluated in the same manner as in Example 1. The evaluation results are shown in the column of "Relative binding activity" in Table 3.

(4) An immobilized support R was obtained in the same manner as in Example 1, except that the cyclic peptide 17 was used instead of the cyclic peptide 1.

(5) The chemical resistance was evaluated in the same manner as in Example 1. The evaluation results are shown in the column of "Chemical resistance" in Table 3.

(6) The stability of the cyclic peptide 17 in the human plasma was evaluated in the same manner as in Example 1. The evaluation results are shown in the column of "Stability in plasma" in Table 3.

Comparative Example 2

(1) A cyclic peptide (SEQ ID NO: 20) represented by Formula (20) was synthesized in the same manner as in Comparative Example 1. Hereinafter, this cyclic peptide will be referred to as "cyclic peptide 18" in some cases.

Asp-[Glu]-Ala-Tyr-His-Leu-Gly-Glu-Leu-Val-Trp-[Lys]-Thr-Lys-Lys (20)

In Formula (20), [Glu] represents an amino acid residue derived from L-glutamic acid, [Lys] represents an amino acid residue derived from L-lysine, and [Glu] and [Lys] are cross-linked to each other through an amide bond formed by dehydrocondensation of a side-chain carboxy group and a side-chain amino group.

(2) An immobilized sensor chip S was obtained in the same manner as in Example 1, except that the cyclic peptide 18 was used instead of the cyclic peptide 1.

(3) The binding activity was evaluated in the same manner as in Example 1. The evaluation results are shown in the column of "Relative binding activity" in Table 3.

(4) An immobilized support S was obtained in the same manner as in Example 1, except that the cyclic peptide 18 was used instead of the cyclic peptide 1.

(5) The chemical resistance was evaluated in the same manner as in Example 1. The evaluation results are shown in the column of "Chemical resistance" in Table 3.

(6) The stability of the cyclic peptide 18 in the human plasma was evaluated in the same manner as in Example 1. The evaluation results are shown in the column of "Stability in plasma" in Table 3.

Comparative Example 3

(1) A cyclic peptide (SEQ ID NO: 21) represented by Formula (21) was synthesized using a full automatic peptide synthesis device (PSSM-8, manufactured by Shimadzu Corporation). Hereinafter, this cyclic peptide will be referred to as "cyclic peptide 19" in some cases.

Asp-[Cys]-Ala-Tyr-His-Arg-Gly-Glu-Leu-Val-Trp-[Cys]-Thr-Lys-Lys (21)

In Formula (21), [Cys] represents an amino acid residue derived from L-cysteine, and two [Cys]'s are cross-linked to each other through a disulfide bond formed by oxidation of side-chain thiol groups (see the following chemical formula).

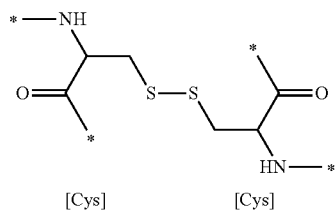 [SMILES: CNC(CSSCC(NC)C(C)=O)C(C)=O]

[Cys]    [Cys]

In the above chemical formula, "*" represents a point of binding to an adjacent amino acid residue.

(2) An immobilized sensor chip T was obtained in the same manner as in Example 1, except that the cyclic peptide 19 was used instead of the cyclic peptide 1.

(3) The binding activity was evaluated in the same manner as in Example 1. The evaluation results are shown in the column of "Relative binding activity" in Table 3.

(4) An immobilized support T was obtained in the same manner as in Example 1, except that the cyclic peptide 19 was used instead of the cyclic peptide 1.

(5) The chemical resistance was evaluated in the same manner as in Example 1. The evaluation results are shown in the column of "Chemical resistance" in Table 3.

RESULTS FROM EXAMPLES•COMPARATIVE EXAMPLES

The following Table 3 shows the results of performance evaluation performed on examples•comparative examples.

TABLE 3

| | | Cyclic peptide | | | Performance evaluation | | |
|---|---|---|---|---|---|---|---|
| | | Name | Cross-linked structure | SEQ ID NO: | Relative binding activity | Chemical resistance | Stability in plasma |
| Example | 1 | Cyclic peptide 1 | Triazole bond | 3 | A | B | A |
| | 2 | Cyclic peptide 2 | Triazole bond | 4 | A | A | A |
| | 3 | Cyclic peptide 3 | Triazole bond | 5 | A | A | — |
| | 4 | Cyclic peptide 4 | Triazole bond | 6 | A | A | A |
| | 5 | Cyclic peptide 5 | Triazole bond | 7 | A | A | — |
| | 6 | Cyclic peptide 6 | Triazole bond | 8 | B | B | — |
| | 7 | Cyclic peptide 7 | Triazole bond | 9 | B | A | — |
| | 8 | Cyclic peptide 8 | Triazole bond | 10 | B | A | — |
| | 9 | Cyclic peptide 9 | Triazole bond | 11 | B | A | — |
| | 10 | Cyclic peptide 10 | Triazole bond | 12 | C | A | — |
| | 11 | Cyclic peptide 11 | Triazole bond | 13 | A | A | — |
| | 12 | Cyclic peptide 12 | Triazole bond | 14 | A | A | — |
| | 13 | Cyclic peptide 13 | Triazole bond | 15 | B | A | — |
| | 14 | Cyclic peptide 14 | Triazole bond | 16 | B | A | — |
| | 15 | Cyclic peptide 15 | Triazole bond | 17 | B | A | — |
| | 16 | Cyclic peptide 16 | Triazole bond | 18 | B | A | — |
| Comparative Example | 1 | Cyclic peptide 17 | Amide bond | 19 | E (standard) | B | E |
| | 2 | Cyclic peptide 18 | Amide bond | 20 | E | B | E |
| | 3 | Cyclic peptide 19 | Disulfide bond | 21 | A | E | — |

<Antibody Binding Properties and Chemical Resistance>

Examples 1 to 16 and Comparative Examples 1 to 3

Examples 1 to 16 were evaluated as C or a higher grade in terms of the relative binding activity and evaluated as B or a higher grade in terms of the chemical resistance. That is, Examples 1 to 16 had sufficient antibody binding properties and excellent chemical resistance. Among these, Examples 2 to 5, 11, and 12 were particularly excellent because they were evaluated as B in terms of both the relative binding activity and the chemical resistance.

In contrast, Comparative Examples 1 and 2 cross-linked through an amide bond were evaluated as B in terms of the chemical resistance and had sufficient chemical resistance. However, Comparative Examples 1 and 2 were evaluated as E in terms of the relative binding activity and had poor antibody binding activity. Furthermore, Comparative Example 3 cross-linked through a disulfide bond was evaluated as A in terms of the relative binding activity and had sufficient antibody binding activity. However, Comparative Example 3 was evaluated as E in terms of the chemical resistance and had poor chemical resistance.

Examples 2, 8, and 10

In Examples 2, 8, and 10, among the amino acid residues in the cross-linked portions, the amino acid residue on the N-terminal side of the polypeptide chain was an amino acid residue [Lys(N3)] derived from ε-azide-L-lysine, and the amino acid residue on the C-terminal side of the polypeptide chain was an amino acid residue [Bpg] derived from L-bishomopropargylglycine (Example 2), an amino acid residue [Hpg] derived from L-homopropargylglycine (Example 8), or an amino acid residue [Pra] derived from L-propargylglycine (Example 10).

Regarding the relative binding activity, Example 2 was evaluated as A, Example 8 was evaluated as B, and Example 10 was evaluated as C. Presumably, in the amino acid residue on the C-terminal side in the cross-linked portion, depending on whether the carbon atom to which a triazole ring is bonded is a δ carbon atom (Example 2), a γ carbon atom (Example 8), or a β carbon atom (Example 10), steric hindrance may exert an influence on the antibody binding site by the triazole ring, and accordingly, the difference in the evaluation results may arise between the above examples.

Examples 7, 11, and 13

In Examples 7, 11, and 13, among the amino acid residues in the cross-linked portions, the amino acid residue on the N-terminal side of the polypeptide chain was an amino acid residue [Abu(N3)] derived from γ-azide-L-homoalanine, and the amino acid residue on the C-terminal side of the polypeptide chain was an amino acid residue [Pra] derived from L-propargylglycine (Example 7), an amino acid residue [Hpg] derived from L-homopropargylglycine (Example 11), or an amino acid residue [Bpg] derived from L-bishomopropargylglycine (Example 13).

Regarding the relative binding activity, Example 11 was evaluated as A, and Examples 7 and 13 were evaluated as B. Presumably, in the amino acid residue on the C-terminal side in the cross-linked portion, depending on whether the carbon atom to which a triazole ring is bonded is a γ carbon atom (Example 11), a β carbon atom (Example 7), or a δ carbon atom (Example 13), steric hindrance of the triazole ring may exert an influence on the antibody binding site, and accordingly, the difference in the evaluation results may arise between the above examples.

Examples 2 and 3, Examples 9 and 10, Examples 11 and 12, and Examples 14 and 16

The cyclic peptide 2 of Example 2 and the cyclic peptide 3 of Example 3 are examples in which the amino acid residue on the N-terminal side and the amino acid residue on the C-terminal side in the cross-linked portion were switched. Furthermore, the cyclic peptide 9 of Example 9 and the cyclic peptide 10 of Example 10, the cyclic peptide 11 of Example 11 and the cyclic peptide 12 of Example 12, and the cyclic peptide 14 of Example 14 and the cyclic peptide 16 of Example 16 are examples in which the amino acid residue on the N-terminal side and the amino acid residue on the C-terminal side in the cross-linked portion were switched. All of Examples 2, 3, 9, 10, 11, 12, 14, and 16 were evaluated as C or a higher grade in terms of the relative binding activity and evaluated as A in terms of the chemical resistance. Accordingly, the antibody binding activity and chemical resistance of these cyclic peptides were sufficient.

Examples 4 and 5

The cyclic peptide 4 of Example 4 and the cyclic peptide 5 of Example 5 are different from each other in terms of whether three lysine residues (one-letter code=K, three-letter code=Lys) having an amino group as an immobilizing functional group are present on the N-terminal or the C-terminal. However, all of Example 4 and Example 5 were evaluated as A in terms of both the relative binding activity and the chemical resistance, and had sufficient antibody binding properties and sufficient chemical resistance. Therefore, it can be said that the amino acid residue having an immobilizing functional group may be present on either the N-terminal side or the C-terminal side.

<<Summary>>

The cyclic peptides (Examples 1 to 10) having a cross-linked structure formed through a triazole ring (triazole bond) were excellent in the antibody binding properties and the chemical resistance. Furthermore, the cyclic peptides (Comparative Example 1 and Comparative Example 2) having a cross-linked structure formed through an amide bond had poor antibody binding properties but exhibited sufficient chemical resistance. It is unclear why the antibody binding properties are poor. Presumably, the rigidity of the amide bond may exert a big influence on the antibody binding properties. The cyclic peptide (Comparative Example 3) having a cross-linked structure formed through a disulfide bond had poor chemical resistance. Presumably, in a case where the cross-linked structure is formed, the ring may be seriously deformed, and the structure may become unstable, and hence the chemical resistance may deteriorate.

<Stability in Plasma>

The cyclic peptide 1 of Example 1, the cyclic peptide 2 of Example 2, and the cyclic peptide 4 of Example 4 were evaluated as A in terms of the stability in the plasma. However, the cyclic peptide 17 of Comparative Example 1 and the cyclic peptide 18 of Comparative Example 2 were evaluated as E in terms of the stability in the plasma.

The above difference of the stability in the plasma results from whether the cross-linked structure is constituted with a triazole bond (Examples 1, 2, and 4) or an amide bond (Comparative Examples 1 and 2).

The cyclic peptide according to the embodiment of the present invention is highly stable in the plasma, and hence the enzyme resistance thereof is excellent. Therefore, the cyclic peptide can be used in the blood. Particularly, the cyclic peptide can be used as a linker for labeling antibodies or a linker for antibody drug conjugates. Furthermore, the cyclic peptide can be stably used even in a reducing atmosphere in a cell.

SEQUENCE LIST

International Patent Application No. 17A135WOW1 based on International Patent Cooperation Treaty, Cyclic Peptide, Affinity ChroJP17029517 20170817----00120067651701728268normal20170815130350201-708151257092040 P1AP10 1_17_12.app

---

What is claimed is:

1. A cyclic peptide represented by Formula (I),

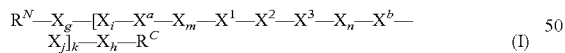

in Formula (I), $R^N$ represents an N-terminal group;

$R^C$ represents a C-terminal group;

$X^1$ represents an L-leucine residue, an L-isoleucine residue, an L-methionine residue, an L-lysine residue, or an L-arginine residue;

$X^2$ represents an L-valine residue or an L-isoleucine residue;

$X^3$ represents an L-tryptophan residue or an L-phenylalanine residue;

one of $X^a$ and $X^b$ represents an amino acid residue derived from an amino acid having an azide group on a side chain and the other represents an amino acid residue derived from an amino acid having an alkynyl group on a side chain, and $X^a$ and $X^b$ are bonded to each other through a triazole bond;

wherein the triazole bond is represented by the following formula,

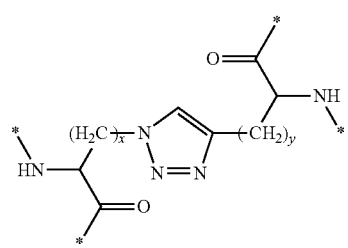

wherein in the formula, * represents a point of binding to an adjacent amino acid residue, x is an integer of 1 to 4, and y is an integer of 1 to 3, $X_g$, $X_h$, $X_i$, $X_j$, $X_m$ and $X_n$ each represent g consecutive X's, h consecutive X's, i consecutive X's, j consecutive X's, m consecutive X's, and n consecutive X's;

X represents an amino acid residue, and in a case where there is a plurality of X's, the plurality of X's may be the same as or different from each other;

g, h, i, and j each independently represent an integer equal to or greater than 0;

m and n are integers satisfying 0≤m≤9, 0≤n≤9, and 3≤m+n 9 simultaneously; and k is an integer equal to or greater than 1, and in a case where k≥2, $X^1$, $X^2$, $X^3$, $X^a$, $X^b$, $X_i$, $X_j$, $X_m$, and $X_n$ in a repeating unit $[X_i—X^a—X_m—X^1—X^2—X^3—X_a—X_n—X^b—X_j]$ each may be the same or different between the repeating units.

2. The cyclic peptide according to claim 1 that is represented by Formula (IA),

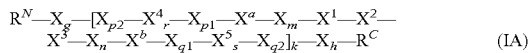
(IA)

in Formula (IA), $R^N$, $R^C$, $X^1$, $X^2$, $X^3$, $X^a$, $X^b$, $X_g$, $X_h$, $X_m$, $X_n$, X, g, h, m, n, and k have the same definitions as those in Formula (I);

$X^4_r$, $X^5_s$, $X_{p1}$, $X_{p2}$, $X_{q1}$, and $X_{q2}$ each represent r consecutive $X^4$'s, s consecutive $X^5$'s, p1 consecutive X's, p2 consecutive X's, q1 consecutive X's, and q2 consecutive X's;

$X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}—X^4_r—X_{p1}—X^a—X_m—X^1—X^2—X^3—X_n—X^b—X_{q1}—X^5_s—X_{q2}]$ each may be the same or different between the repeating units.

3. The cyclic peptide according to claim 1 that is represented by Formula (IB),

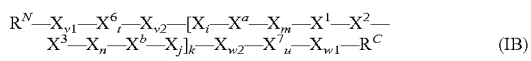
(IB)

in Formula (IB), $R^N$, $R^C$, $X^1$, $X^2$, $X^3$, $X^a$, $X^b$, $X_i$, $X_j$, $X_m$, $X_n$, X, i, j, m, n, and k have the same definitions as those in Formula (I);

$X^6_t$, $X^7_u$, $X_{v1}$, $X_{v2}$, $X_{w1}$, and $X_{w2}$ each represent t consecutive $X^6$'s, u consecutive $X^7$'s, v1 consecutive X's, v2 consecutive X's, w1 consecutive X's, and w2 consecutive X's;

$X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other;

t and u each represent an integer satisfying 0≤t≤5, 0≤u≤5, and 1≤Max (t,u)≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≤2, $X^1$, $X^2$, $X^3$, $X^a$, $X^b$, $X_i$, $X_j$, $X_m$, and $X_n$ in a repeating unit $[X_i—X^a—X_m—X^1—X^2—X^3—X_n—X^b—X_j]$ each may be the same or different between the repeating units.

4. The cyclic peptide according to claim 1 that is represented by Formula (IC),

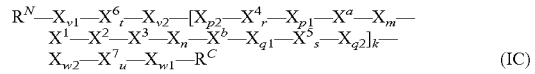
(IC)

in Formula (IC), $R^N$, $R^C$, $X^1$, $X^2$, $X^3$, $X^a$, $X^b$, $X_m$, $X_n$, X, m, n, and k have the same definitions as those in Formula (I);

$X_{p1}$, $X_{p2}$, $X_{q1}$, $X_{q2}$, $X^4_r$, $X^5_s$, $X^6_t$, $X^7_u$, $X_{v1}$, $X_{v2}$, $X_{w1}$, and $X_{w2}$ each represent p1 consecutive X's, p2 consecutive X's, q1 consecutive X's, q2 consecutive X's, r consecutive $X^4$'s, s consecutive $X^5$'s, t consecutive $X^6$'s, u consecutive $X^7$'s, v1 consecutive X's, v2 consecutive X's, w1 consecutive X's, and w2 consecutive X's;

$X^4$ and $X^5$ each independently represent an amino acid residue derived from an amino acid having a carboxy group on a side chain or an amino acid residue derived from an amino acid having a hydroxy group on a side chain, and in a case where there is a plurality of $X^4$'s or $X^5$'s, the plurality of $X^4$'s or $X^5$'s may be the same as or different from each other;

$X^6$ and $X^7$ each independently represent an amino acid residue derived from an amino acid having an immobilizing functional group on a side chain, and in a case where there is a plurality of $X^6$'s or $X^7$'s, the plurality of $X^6$'s or $X^7$'s may be the same as or different from each other;

p1, p2, q1, and q2 each independently represent an integer equal to or greater than 0;

r and s each represent an integer satisfying 0≤r≤5, 0≤s≤5, and 1≤Max (r,s)≤5, where Max (r,s) represents a larger one between two numbers represented by r and s in a case where r≠s and represents r or s in a case where r=s; and t and u each represent an integer satisfying 0≤t≤5, 0≤u≤5, and 1≤Max (t,u)≤5, where Max (t,u) represents a larger one between two numbers represented by t and u in a case where t≠u and represents t or u in a case where t=u;

v1, v2, w1, and w2 each independently represent an integer equal to or greater than 0; and in a case where k≥2, $X^1$, $X^2$, $X^3$, $X^a$, $X^b$, $X^4_r$, $X^5_s$, $X_m$, $X_n$, $X_{p2}$, $X_{p1}$, $X_{q1}$, and $X_{q2}$ in a repeating unit $[X_{p2}—X^4_r—X_{p1}—X^a—X_m—X^1—X^2—X^3—X_n—X^b—X_{q1}—X^5_s—X_{q2}]$ each may be the same or different between the repeating units.

5. The cyclic peptide according to claim 2, wherein the amino acid having a carboxy group on a side chain is at least one of amino acid selected from the group consisting of L-aspartic acid, D-aspartic acid, L-glutamic acid, D-glutamic acid, L-homoglutamic acid, and D-homoglutamic acid, and the amino acid having a hydroxy group on a side chain is at least one of amino acid selected from the group consisting of L-serine, D-serine, L-homoserine, D-homoserine, L-tyrosine, D-tyrosine, L-threonine, D-threonine, L-allothreonine, and D-allothreonine.

6. The cyclic peptide according to claim 3, wherein the amino acid having an immobilizing functional group on a side chain is at least one of amino acid selected from the group consisting of L-lysine, D-lysine, L-cysteine, D-cysteine, L-homocysteine, and D-homocysteine.

7. The cyclic peptide according to claim 1,
wherein the amino acid having an azide group on a side chain is at least one of amino acid selected from the group consisting of β-azide-L-alanine, γ-azide-L-homoalanine, δ-azide-L-norvaline, and ε-azide-L-lysine, and the amino acid having an alkynyl group on a side chain is at least one of amino acid selected from the group consisting of L-propargylglycine, L-homopropargylglycine, and L-bishomopropargylglycine.

8. The cyclic peptide according to claim 1,
wherein $X_m$—$X^1$—$X^2$—$X^3$—$X_n$ and an amino acid sequence (SEQ ID NO: 1) represented by Formula (1) or an amino acid sequence (SEQ ID NO: 2) represented by Formula (2) share sequence homology equal to or higher than 70%,

A-Y—H-L$^1$-G-E-L$^2$-V—W  (1)

A-Y—H—R-G-E-L$^2$-V—W  (2)

in Formula (1) and Formula (2),
A represents an L-alanine residue or a D-alanine residue;
Y represents an L-tyrosine residue or a D-tyrosine residue;
H represents an L-histidine residue or a D-histidine residue;
L$^1$ represents an L-leucine residue or a D-leucine residue;
R represents an L-arginine residue or a D-arginine residue;
G represents a glycine residue;
E represents an L-glutamic acid residue or a D-glutamic acid residue;
L$^2$ represents an L-leucine residue;
V represents an L-valine residue; and
W represents an L-tryptophan residue.

9. The cyclic peptide according to claim 1, wherein k=1.

10. The cyclic peptide according to claim 1 that is represented by Formula (II), $R^N$—$X_{v0}$—$X^6_{t0}$—$X_{e0}$—$X^4_{r0}$—$X_{p0}$—$X^a$-A-Y—H—$X^8$-G-E-L-V—W—$X^b$—$X_{q0}$—$X^5_{s0}$—$X_{f0}$—$X^7_{u0}$—$X_{w0}$—$R^C$  (II)

in Formula (II),
$X^a$, $X^b$, X, $R^N$, and $R^C$ have the same definitions as those in Formula (I);
$X^4$ and $X^5$ each independently represent an L-amino acid residue or a D-amino acid residue having a carboxy group or a hydroxy group on a side chain, and in a case where there is a plurality of $X^4$'s or $X^5$'s, the plurality of $X^4$'s or $X^5$'s may be the same as or different from each other;
$X^6$ and $X^7$ each independently represent an L-amino acid residue or a D-amino acid residue having an immobilizing functional group on a side chain, and in a case where there is a plurality of $X^6$'s or $X^7$'s, the plurality of $X^6$'s or $X^7$'s may be the same as or different from each other;

$X^8$ represents any one residue selected from the group consisting of an L-leucine residue, an L-arginine residue, a D-leucine residue, and a D-arginine residue;
e0 and f0 each represent an integer satisfying 0≤e0≤10 and 0≤f0≤10;
p0 and q0 each represent an integer satisfying 0≤p0≤5 and 0≤q0≤5;
r0 and s0 each represent an integer satisfying 0≤r0≤5 and 0≤s0≤5;
t0 and u0 each represent an integer satisfying 0≤t0≤5 and 0≤u0≤5;
v0 and w0 each represent an integer satisfying 0≤v0≤5 and 3≤w0≤5;
p0, q0, r0, s0, t0, u0, v0, and w0 satisfy 0≤p0+q0+r0+s0+t0+u0+v0+w0≤39;
A represents an L-alanine residue or a D-alanine residue;
Y represents an L-tyrosine residue or a D-tyrosine residue;
H represents an L-histidine residue or a D-histidine residue;
G represents a glycine residue;
E represents an L-glutamic acid residue or a D-glutamic acid residue;
L represents an L-leucine residue;
V represents an L-valine residue; and
W represents an L-tryptophan residue.

11. An affinity chromatography support comprising:
a water insoluble carrier; and
the cyclic peptide according to claim 1,
wherein the water insoluble carrier and the cyclic peptide are directly or indirectly bonded to each other.

12. A labeled antibody comprising:
an antibody;
a labeling compound; and
the cyclic peptide according to claim 1,
wherein the antibody and the labeling compound are bonded to each other through the cyclic peptide.

13. An antibody drug conjugate comprising:
an antibody;
a drug; and
the cyclic peptide according to claim 1,
wherein the antibody and the drug are bonded to each other through the cyclic peptide.

14. The antibody drug conjugate according to claim 13,
wherein the drug is a drug having undergone liposomization, polymer micellization, or PEGylation.

15. A pharmaceutical preparation comprising:
a drug; and
the cyclic peptide according to claim 1,
wherein the drug and the cyclic peptide are directly or indirectly bonded to each other.

16. The pharmaceutical preparation according to claim 15,
wherein the drug is a drug having undergone liposomization, polymer micellization, or PEGylation.

* * * * *

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Partial peptide 1: A-Y-H-L-G-E-L-V-W

<400> SEQUENCE: 1

Ala Tyr His Leu Gly Glu Leu Val Trp
1               5

<210> SEQ ID NO 2
<211> LENGTH: 9
<212> TYPE: PRT
<213> ORGANISM: Artificial Sequence
<220> FEATURE:
<223> OTHER INFORMATION: Partial peptide 2: A-Y-H-R-G-E-L-V-W

<400> SEQUENCE: 2

Ala Tyr His Arg Gly Glu Leu Val Trp
1               5

<210> SEQ ID NO 3
<211> LENGTH: 15
<212> TYPE: PRT
<213> ORGANISM: Artificial Sequence
<220> FEATURE:
```

```
<223> OTHER INFORMATION: Cyclic peptide 1: D-(Lys(N3))-A-Y-H-R-G-E-L-V-
      W-(Bpg)-T-K-K A triazole bond is formed between (Lys(N3)) and
      (Bpg). (Lys(N3)): epsilon-azido-L-lysine residue
      (Bpg): L-bishomopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from epsilon-azido-L-lysine
      Xaa12: induced from L-bishomopropargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from epsilon-azido-L-lysine
      Xaa12: induced from L-bishomopropargylglycine

<400> SEQUENCE: 3

Asp Xaa Ala Tyr His Arg Gly Glu Leu Val Trp Xaa Thr Lys Lys
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Cyclic peptide 2: D-(Lys(N3))-A-Y-H-L-G-E-L-V-
      W-(Bpg)-T-K-K A triazole bond is formed between (Lys(N3)) and
      (Bpg). (Lys(N3)): epsilon-azido-L-lysine residue
      (Bpg): L-bishomopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from epsilon-azido-L-lysine
      Xaa12: induced from L-bishomopropargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from epsilon-azido-L-lysine
      Xaa12: induced from L-bishomopropargylglycine

<400> SEQUENCE: 4

Asp Xaa Ala Tyr His Leu Gly Glu Leu Val Trp Xaa Thr Lys Lys
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Cyclic peptide 3: D-(Bpg)-A-Y-H-L-G-E-L-V-W-
      (Lys(N3))-T-K-K A triazole bond is formed between (Bpg) and
      (Lys(N3)). (Bpg): L-bishomopropargylglycine residue
      (Lys(N3)): epsilon-azido-L-lysine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from L-bishomopropargylglycine
      Xaa12: induced from epsilon-azido-L-lysine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from L-bishomopropargylglycine
      Xaa12: induced from epsilon-azido-L-lysine

<400> SEQUENCE: 5

Asp Xaa Ala Tyr His Leu Gly Glu Leu Val Trp Xaa Thr Lys Lys
1               5                   10                  15
```

<210> SEQ ID NO 6
<211> LENGTH: 15
<212> TYPE: PRT
<213> ORGANISM: Artificial Sequence
<220> FEATURE:
<223> OTHER INFORMATION: Cyclic peptide 4: D-(Hpg)-A-Y-H-L-G-E-L-V-W-
(Ala(N3))-T-K-K A triazole bond is formed between (Hpg) and
(Ala(N3)). (Hpg): L-homopropargylglycine residue
(Ala(N3)): beta-azido-L-alanine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
Xaa2: induced from L-homopropargylglycine
Xaa12: induced from beta-azido-L-alanine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
Xaa2: induced from L-homopropargylglycine
Xaa12: induced from beta-azido-L-alanine

<400> SEQUENCE: 6

Asp Xaa Ala Tyr His Leu Gly Glu Leu Val Trp Xaa Thr Lys Lys
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Cyclic peptide 5: K-K-K-D-(Hpg)-A-Y-H-L-G-E-L-
V-W-(Ala(N3))-T  A triazole bond is formed between (Hpg) and
(Ala(N3)). (Hpg): L-homopropargylglycine residue
(Ala(N3)): beta-azido-L-alanine residue
<220> FEATURE:
<221> NAME/KEY: MISC_FEATURE
<222> LOCATION: (5)..(5)
<223> OTHER INFORMATION: Xaa5 and Xaa15 are bridged by a triazole bond.
Xaa5: induced from L-homopropargylglycine
Xaa15: induced from beta-azido-L-alanine
<220> FEATURE:
<221> NAME/KEY: MISC_FEATURE
<222> LOCATION: (15)..(15)
<223> OTHER INFORMATION: Xaa5 and Xaa15 are bridged by a triazole bond.
Xaa5: induced from L-homopropargylglycine
Xaa15: induced from beta-azido-L-alanine

<400> SEQUENCE: 7

Lys Lys Lys Asp Xaa Ala Tyr His Leu Gly Glu Leu Val Trp Xaa Thr
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Cyclic peptide 6: D-(Abu(N3))-A-Y-H-R-G-E-L-V-
W-(Pra)-T-K-K A triazole bond is formed between (Abu(N3)) and
(Pra). (Abu(N3)) : gamma-azido-L-homoalanine residue
(Pra): L-propargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
Xaa2: induced from gamma-azido-L-homoalanine
Xaa12: induced from L-propargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
Xaa2: induced from gamma-azido-L-homoalanine
Xaa12: induced from L-propargylglycine

<400> SEQUENCE: 8

```
Asp Xaa Ala Tyr His Arg Gly Glu Leu Val Trp Xaa Thr Lys Lys
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Cyclic peptide 7: D-(Abu(N3))-A-Y-H-L-G-E-L-V-
      W-(Pra)-T-K-K A triazole bond is formed between (Abu(N3)) and
      (Pra). (Abu(N3)): gamma-azido-L-homoalanine residue
      (Pra): L-propargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from gamma-azido-L-homoalanine
      Xaa12: induced from L-propargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from gamma-azido-L-homoalanine
      Xaa12: induced from L-propargylglycine

<400> SEQUENCE: 9

Asp Xaa Ala Tyr His Leu Gly Glu Leu Val Trp Xaa Thr Lys Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Cyclic peptide 8: D-(Lys(N3))-A-Y-H-L-G-E-L-V-
      W-(Hpg)-T-K-K A triazole bond is formed between (Lys(N3)) and
      (Hpg). (Lys(N3)): epsilon-azido-L-lysine residue
      (Hpg): L-homopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from epsilon-azido-L-lysine
      Xaa12: induced from L-homopropargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from epsilon-azido-L-lysine
      Xaa12: induced from L-homopropargylglycine

<400> SEQUENCE: 10

Asp Xaa Ala Tyr His Leu Gly Glu Leu Val Trp Xaa Thr Lys Lys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Cyclic peptide 9: D-(Pra)-A-Y-H-L-G-E-L-V-W-
      (Lys(N3))-T-K-K A triazol bond is formed between (Pra) and
      (Lys(N3)). (Pra): L-propargylglycine residue
      (Lys(N3)): epsilon-azido-L-lysine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from L-propargylglycine
      Xaa12: induced from epsilon-azido-L-lysine
<220> FEATURE:
<221> NAME/KEY: MISC_FEATURE
<222> LOCATION: (12)..(12)
```

-continued

```
<223> OTHER INFORMATION: Xaa2 and Xaa12 are bridged by a triazole bond.
      Xaa2: induced from L-propargylglycine
      Xaa12: induced from epsilon-azido-L-lysine

<400> SEQUENCE: 11

Asp Xaa Ala Tyr His Leu Gly Glu Leu Val Trp Xaa Thr Lys Lys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Cyclic peptide 10: D-(Lys(N3))-A-Y-H-L-G-E-L-V-
      W-(Pra)-T-K-K A triazole bond is formed between (Lys(N3)) and
      (Pra). (Lys(N3)): epsilon-azido-L-lysine residue
      (Pra): L-propargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from epsilon-azido-L-lysine
      Xaa12: induced from L-propargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from epsilon-azido-L-lysine
      Xaa12: induced from L-propargylglycine

<400> SEQUENCE: 12

Asp Xaa Ala Tyr His Leu Gly Glu Leu Val Trp Xaa Thr Lys Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Cyclic peptide 11: D-(Abu(N3))-A-Y-H-L-G-E-L-V-
      W-(Hpg)-T-K-K A tiazole bond is formed between (Abu(N3)) and
      (Hpg). (Abu(N3)): gamma-azido-L-homoalanine residue
      (Hpg): L-homopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from gamma-azido-L-homoalanine
      Xaa12: induced from L-homopropargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from gamma-azido-L-homoalanine
      Xaa12: induced from L-homopropargylglycine

<400> SEQUENCE: 13

Asp Xaa Ala Tyr His Leu Gly Glu Leu Val Trp Xaa Thr Lys Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Cyclic peptide 12: D-(Hpg)-A-Y-H-L-G-E-L-V-W-
      (Abu(N3))-T-K-K (Hpg): L-homopropargylglycine residue
      (Abu(N3)): gamma-azido-L-homoalanine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from L-homopropargylglycine
```

```
      Xaa12: induced from gamma-azido-L-homoalanine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from L-homopropargylglycine
      Xaa12: induced from gamma-azido-L-homoalanine

<400> SEQUENCE: 14

Asp Xaa Ala Tyr His Leu Gly Glu Leu Val Trp Xaa Thr Lys Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Cyclic peptide 13: D-(Abu(N3))-A-Y-H-L-G-E-L-V-
      W-(Bpg)-T-K-K (Abu(N3)): gamma-azido-L-homoalanine residue
      (Bpg): L-bishomopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from gamma-azido-L-homoalanine
      Xaa12: induced from L-bishomopropargylglycine
<220> FEATURE:
<221> NAME/KEY: MISC_FEATURE
<222> LOCATION: (12)..(2)
<223> OTHER INFORMATION: Xaa2 and Xaa12 are bridged by a triazole bond.
      Xaa2: induced from gamma-azido-L-homoalanine
      Xaa12: induced from L-bishomopropargylglycine
<220> FEATURE:
<221> NAME/KEY: misc_feature
<222> LOCATION: (12)..(12)
<223> OTHER INFORMATION: Xaa can be any naturally occurring amino acid

<400> SEQUENCE: 15

Asp Xaa Ala Tyr His Leu Gly Glu Leu Val Trp Xaa Thr Lys Lys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Cyclic peptide 14: D-(Bpg)-A-Y-H-L-G-E-L-V-W-
      (Nva(N3))-T-K-K (Bpg): L-bishomopropargylglycine residue
      (Nva(N3)): delta-azido-L-norvaline residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
      Xaa2: induced from gamma-azido-L-homoalanine
      Xaa12: induced from delta-azido-L-norvaline
<220> FEATURE:
<221> NAME/KEY: MISC_FEATURE
<222> LOCATION: (12)..(12)
<223> OTHER INFORMATION: Xaa2 and Xaa12 are bridged by a triazole bond.
      Xaa2: induced from gamma-azido-L-homoalanine
      Xaa12: induced from delta-azido-L-norvaline

<400> SEQUENCE: 16

Asp Xaa Ala Tyr His Leu Gly Glu Leu Val Trp Xaa Thr Lys Lys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Cyclic peptide 15: D-(Hpg)-A-Y-H-L-G-E-L-V-W-
      (Nva(N3))-T-K-K (Hpg): L-homopropargylglycine residue
```

(Nva(N3)): delta-azido-L-norvaline residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
    Xaa2: induced from L-homopropargylglycine
    Xaa12: induced from delta-azido-L-norvaline
<220> FEATURE:
<221> NAME/KEY: MISC_FEATURE
<222> LOCATION: (12)..(12)
<223> OTHER INFORMATION: Xaa2 and Xaa12 are bridged by a triazole bond.
    Xaa2: induced from L-homopropargylglycine
    Xaa12: induced from delta-azido-L-norvaline

<400> SEQUENCE: 17

Asp Xaa Ala Tyr His Leu Gly Glu Leu Val Trp Xaa Thr Lys Lys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Cyclic peptide 16: D-(Nva(N3))-A-Y-H-L-G-E-L-V-
    W-(Bpg)-T-K-K (Nva(N3)): delta-azido-L-norvaline residue
    (Bpg): L-bishomopropargylglycine residue
<220> FEATURE:
<221> NAME/KEY: MISC_FEATURE
<222> LOCATION: (2)..(2)
<223> OTHER INFORMATION: Xaa2 and Xaa12 are bridged by a triazole bond.
    Xaa2: induced from  delta-azido-L-norvaline
    Xaa12: induced from L-bishomopropargylglycine
<220> FEATURE:
<221> NAME/KEY: MISC_FEATURE
<222> LOCATION: (12)..(12)
<223> OTHER INFORMATION: Xaa2 and Xaa12 are bridged by a triazole bond.
    Xaa2: induced from  delta-azido-L-norvaline
    Xaa12: induced from L-bishomopropargylglycine

<400> SEQUENCE: 18

Asp Xaa Ala Tyr His Leu Gly Glu Leu Val Trp Xaa Thr Lys Lys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Cyclic peptide 17: D-(Glu)-A-Y-H-R-G-E-L-V-W-
    (Lys)-T-K-K An amide bond is formed between (Glu) and (Lys).
    (Glu): L-glutamic acid residue
    (Lys): L-lysine residue
<220> FEATURE:
<221> NAME/KEY: MISC_FEATURE
<222> LOCATION: (2)..(2)
<223> OTHER INFORMATION: Glu2 and Lys12 are brigded by an amide bond.
<220> FEATURE:
<221> NAME/KEY: MISC_FEATURE
<222> LOCATION: (12)..(12)
<223> OTHER INFORMATION: Glu2 and Lys12 are brigded by an amide bond.

<400> SEQUENCE: 19

Asp Glu Ala Tyr His Arg Gly Glu Leu Val Trp Lys Thr Lys Lys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Cyclic peptide 18: D-(Glu)-A-Y-H-L-G-E-L-V-W-
    (Lys)-T-K-K An amide bond is formed between (Glu) and (Lys).
    (Glu): L-glutamic acid residue

```
                (Lys): L-lysine residue
<220> FEATURE:
<221> NAME/KEY: MISC_FEATURE
<222> LOCATION: (2)..(2)
<223> OTHER INFORMATION: Glu2 and Lys12 are brigded by an amide bond.
<220> FEATURE:
<221> NAME/KEY: MISC_FEATURE
<222> LOCATION: (12)..(12)
<223> OTHER INFORMATION: Glu2 and Lys12 are brigded by an amide bond.

<400> SEQUENCE: 20

Asp Glu Ala Tyr His Arg Gly Glu Leu Val Trp Lys Thr Lys Lys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Cyclic peptide 19: D-(Cys)-A-Y-H-R-G-E-L-V-W-
      (Cys)-T-K-K A disulfide bond is formed between (Cys) and (Cys).
      (Cys): L-cysteine residue
<220> FEATURE:
<221> NAME/KEY: MISC_FEATURE
<222> LOCATION: (2)..(2)
<223> OTHER INFORMATION: Cys2 and Cys 12 are bridged by a disulfide
      bond.
<220> FEATURE:
<221> NAME/KEY: MISC_FEATURE
<222> LOCATION: (12)..(12)
<223> OTHER INFORMATION: Cys2 and Cys 12 are bridged by a disulfide
      bond.

<400> SEQUENCE: 21

Asp Cys Ala Tyr His Arg Gly Glu Leu Val Trp Cys Thr Lys Lys
1               5                   10                  15

<210> SEQ ID NO 22
<211> LENGTH: 9
<212> TYPE: PRT
<213> ORGANISM: Artificial Sequence
<220> FEATURE:
<223> OTHER INFORMATION: Partial peptide 1: A-W-H-L-G-E-L-V-W

<400> SEQUENCE: 22

Ala Trp His Leu Gly Glu Leu Val Trp
1               5
```